United States Patent
Toscani et al.

(10) Patent No.: US 6,410,825 B1
(45) Date of Patent: Jun. 25, 2002

(54) A-MYB NULL MUTANT TRANSGENIC MICE

(75) Inventors: Antonio Toscani, deceased, late of Philadelphia, PA (US); by Donato Toscani, heir; by Amelia Toscani, heir, both of Teramo (IT); Kimi Hatton, Fairfax, VA (US); E. Premkumar Reddy, Villanova, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/402,929

(22) PCT Filed: Apr. 7, 1998

(86) PCT No.: PCT/US98/06896

§ 371 (c)(1),
(2), (4) Date: Mar. 22, 2000

(87) PCT Pub. No.: WO98/46726

PCT Pub. Date: Oct. 22, 1998

Related U.S. Application Data

(60) Provisional application No. 60/043,353, filed on Apr. 15, 1997.

(51) Int. Cl.$^7$ .................. A01K 67/00; C12N 15/85; C12N 15/09
(52) U.S. Cl. .................. 800/18; 800/8; 800/13; 800/21; 435/325; 435/455
(58) Field of Search .................. 536/23.1; 800/8, 800/21, 13, 14, 15, 16, 17, 18, 19, 20; 435/325, 455

(56) References Cited

FOREIGN PATENT DOCUMENTS

| EP | WO 94/06908 | * | 3/1994 |
| EP | WO 95/11968 | * | 5/1995 |

OTHER PUBLICATIONS

Mansour et al., Disruption of the proto–oncogene int–3 in mouse . . . , Nov. 24, 1988, Nature, vol. 336.*

Mettus et al., Murine A–myb: evidence for differential splicing and tissue–specific expression, Aug. 1994, Oncogene, vol. 9, pp. 3077–3086.*

Mullins et al., Perpectives Series: Molecular Medicine in Genetically Engineered Animals, Apr. 1, 1996, J. Clin. Invest., vol. 98, No. 11, pp. S37–S40.*

Moreadith et al., Gene targeting in embryonic stem cells: the new physiology and metabolism, 1997, J. Mol. Med., vol. 75, pp. 208–216.*

Sleeman, "Xenopus A–myb is expressed during early spermatogenesis", *Oncogene*, 8: 1931–1941 (1993).*

Trauth, et al., "Mouse A–myb encodes a trans–activator and its expressed in mitotically active cells of the developing central nervous system, adult testis and B lymphocytes", *EMBO J.*, 13: 5994–6005 (1994).*

Nomura et al., "Isolation of human cDNA clones of myb–related genes, A–myb and B–myb", *Nucl. Acids Res.*, 16: 110750–11089 (1988).*

Golay et al., "The human A–myb protein is a strong sctivator of transcription", *Oncogene*, 9: 2469–2479 (1994).*

Mettus et al., "Murine A–myb: evidence of differential splicing and tissue–specific expression", *Oncogene*, 9L 3077–3086 (1994).*

Bradley, et al., "Modifying The Mouse: Design and Desire", *Bio/Technology*, 10: 534–539 (1992).*

Latham et al., "Temporal patterns of A–myb and B–myb gene expression during testis development", *Oncogene*, 13:1661–1168 (1996).*

Mucenski et al. "A Functional c–myb Gene Is Required for Normal Murine Fetal Hepatic Hematopoiesis", *Cell*, 65:677–689 (May 1991).*

Toscani et al., "Arrest of spermatogenesis and defective breast development in mice lacking A–myb", *Nature*, 386:713–716 (Apr. 1997).*

\* cited by examiner

Primary Examiner—Michael C. Wilson
(74) Attorney, Agent, or Firm—Drinker Biddle & Reath LLP

(57) ABSTRACT

Transgenic non-human animals and transgenic non-human stem cells are described having a functionally disrupted A-myb locus. Targeting constructs used to produce such transgenic stem cells and animals, and methods and targeting constructs for inactivating an endogenous A-myb gene locus, are also provided. Also provided are methods for generating transgenic sperm and transgenic nonhuman animals harboring a desired transgene.

8 Claims, 8 Drawing Sheets

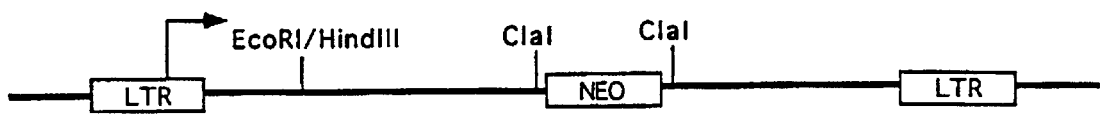
FIG. 9A
pMV-7 Δ ClaI/neo E/H
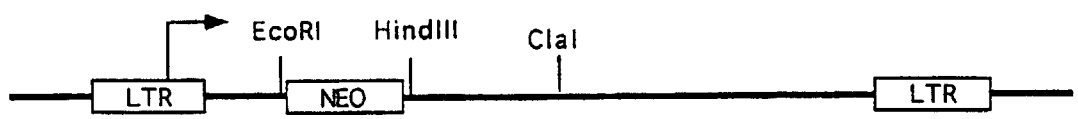
FIG. 9B
pMV-7 Δ ClaI/neo E/H-A-myb
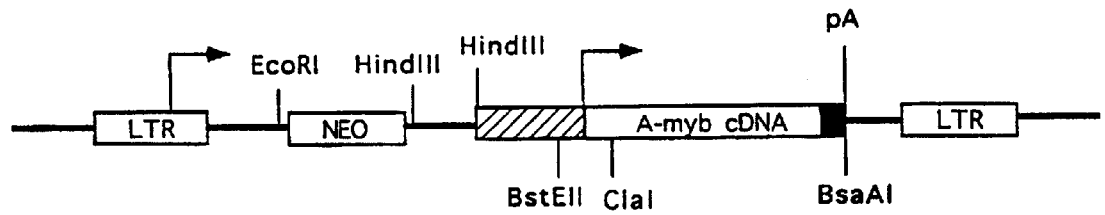
 - A-myb promoter  FIG. 9C
■ BGH pA signal

SEQUENCE LISTING (1) GENERAL INFORMATION:

(iii) NUMBER OF SEQUENCES: 7

-continued (2) INFORMATION FOR SEQ ID NO:1:

(i) SEQUENCE CHARACTERISTICS:
        (A) LENGTH: 3602 base pairs
        (B) TYPE: nucleic acid
        (C) STRANDEDNESS: single
        (D) TOPOLOGY: linear (xi) SEQUENCE DESCRIPTION: SEQ ID NO:1:

```
CCAGCACGCC TCCTGACATG TCCAGGGCAT CCCTGGCCGG GCCCGCCGCG G CTAGGAGCA      60
GTGGGTCTTG GTCCGCCCCT CTGTCCCTCA GTCCCGCCTG GCCCTGACCT G ACCGGGCCT    120
GCTTTCCGCT CTCGGTCACC TGAGGGAAGG AGTTGGGGAA GCGGCGGGTG G GTCTCGGAG    180
AGGGAGCATT GGCCCCAGGC TGGAGGAGGC TGACCCCGCG TCCCCGCCCA G CCCGCGCCT    240
ATGCGGTACT TGAAGGATGG CGAAGAGGTC GCGCAGTGAG GACGAGGATG A TGACCTTCA    300
ATATGCTGAT CATGATTATG AAGTACCTCA ACAAAAGGA CTGAAAAAAC T CTGGAACAG     360
AGTAAAATGG ACAAGAGATG AGGATGACAA GTTAAAGAAG TTGGTTGAAC A ACACGGAAC    420
TGATGATTGG ACTCTAATTG CTAGTCATCT TCAAAATCGT TCTGATTTTC A GTGCCAACA    480
TCGATGGCAG AAGGTTTTAA ATCCAGAATT GATAAAGGGT CCTTGGACTA A GGAAGAAGA    540
TCAGAGGGTT ATTGAATTAG TTCAGAAATA TGGGCCAAAA AGGTGGTCTT T AATTGCAAA    600
ACATTTAAAA GGAAGAATAG GCAAGCAGTG CAGAGAAAGA TGGCACAATC A CCTGAACCC    660
TGAAGTGAAG AAGTCTTCCT GGACAGAAGA AGAAGACAGG ATCATATATG A AGCACACAA    720
GCGCCTGGGA AACCGTTGGG CCGAGATTGC TAAGTTACTT CCTGGAAGGA C TGATAATTC    780
TATCAAAAAT CATTGGAATT CTACCATGCG AAGAAAAGTG GAACAGGAGG G CTATTTACA    840
AGATGGAATA AAATCAGAGC GGTCTTCATC AAAACTTCAA CACAAACCTT G TGCGACTAT    900
GGACCATTTG CAAACCCAGA ATCAGTTTTA CATTCCTGTT CAGATCCCTG G GTATCAGTA    960
TGTGTCGCCT GATGGCAATT GTGTTGAACA TGTTCAGACA TCTGCCTTTA T TCAGCAACC   1020
CTTTGTTGAT GAAGATCCTG ATAAAGAAAA AAAAATAAAG GAGCTCGAGT T GCTTCTTAT   1080
GTCAGCCGAG AATGAAGTTA GAAGGAAGAG GCTTCCACCT CAACCTGGAA G CTTTTCTAG   1140
CTGGTCTGGT AGTTTCCTCA TGGATGATAG TATGTCTAAC ACACTGAATA A TCTGGAGGA   1200
ACACACTACT GAGTTTTATA GCATGGATGA AAATCAAACT GTTTCTGCTC A GCAGAATTC   1260
ACCCACAAAG TTTCTAGCTG TAGAAGCAAA TGCTGTGCTG TCTTCTCTAC A GACCATCCC   1320
AGAATTCGCA GAAACTCTGG AATTAATTGA ATCGGATCCT GTAGCATGGA G TGATGTTAC   1380
CAGTTTTGAT CTTTCTGATG CTGCTGCTTC TCCTGTCAAG TCTACTCCAG T TAAATTAAT   1440
GAGAATTCAA CATAATGAAG GAGCCATGGA ATGCCAGTTT AACGTCAGTC T TGTACTTGA   1500
AGGGAAAAAG AACAGTCGTA ATGGTGGAGA CAGTGAAGCT ATTCCTTTAA C ATCCCCAAA   1560
TGTGGTCAAG TTTAGCACTC CTCCAACCAT CCTCAGAAAA AAGAAAAGAA T TCGAGTGGG   1620
TCAGTCTGCA GGCAGTGAGC TTGGCGATGG CTCACTTAGC GAAGTTGGTA A TGCAGCACT   1680
CAAACACACA CCAGTGAAAA CACTACCATT TTCTCCTTCT CAGTTTTTTA A CACATGTCC   1740
TGGAAATGAA CAACTTAATA TAGAAAACCC TTCCTTTACA TCAACCCCAA T TTGTGGGCA   1800
GAAAGTTCTC ATTACAACTC CTCTTCAGAA GGAAGCAACC CCCAAAGATC A AAAGAAAA   1860
TGTAGGATTC AGAACTCCTA CTATTAGAAG ATCTATACTG GCACCACAC C AAGAACTCC   1920
TACTCCTTTT AAGAATGCAC TTGCTGCTCA GGAAAAAAAA TATGGACCTC T TAAAATTGT   1980
GTCCCAGCCA CTTGCCTTTT TGGAAGAAGA CATTCGAGAA GTTTTAAAAG A GAAACTGG   2040
AACAGATATA TTCCTCAAAG AGGAAGATGA ACCTGCTTAT AAAAGCTGCA A ACAGGAGCA   2100
```

-continued

```
CTCTGCATCT GTGAAGAAGG TCAGAAAATC CCTTGCCTTA GAGAGCTGGG A CAAAGAAGA    2160

ACCAGGGACT CAACTGCTAA CTGAAGACAT TCAGACATG CAGTCAGAAA A TATTCTTAC    2220

AACATCTTTA TTAATGATAC CATTATTGGA AATACATGAC AATAGGTGCA A CTTGACTCC    2280

TGAAAAACAA GATATAAATT CAGCCAACAA AACATATACA CTTAATAAAA A GAGACCAAA    2340

CCCTAACCCT TGTAAAGCTG TCAAATTGGA AAAGAGTCTT CAGTCAAATT G TGAATGGGA    2400

AACAGTGGTA TATGGGAAGA CAGAAGACCA ACTTATCATG ACTGAACAAG C GAGAAGATA    2460

TCTGAGTACT TACACAGCTA CCAGCAGCAC ATCAAGAGCT CTAATACTCT A ACTGTTACT    2520

AAAGCTGATA AAATGCCCTA CCCCTTTACT GTATTTTATG CTAAATTAGG T TGCAATGAA    2580

ATTTGTCTCA ATTAATTCTT TTAAAGGTTT TAATACATCC CTAAAATGGT T CACGTTTTT    2640

TTCTATATTG AACAGGCAAA AAACTAATAA GCTACTTAAA GTAAGGGGTA G GCAAATTTA    2700

TTATTTATAT GTTAAGAAAA TGAGAGTTTT AAAATTTGTT TTAAAGAACA A AATGGGAAA    2760

ATAAGCATGT TTCTGGATAT TCCATAGTAA ATTCTCACAT AATTTCTTTA C AGGATATAT    2820

GTTGCTACTG TCTCAAGGCT GTAGTCTGTT ATAAACAAGT TAAGTATGTG T GACCTCTGA    2880

AAGTCTACAT TTAGGAAGCA CAGAGGCTTT ATGAAGTACT TTTGCATGTG T GCTGATTTA    2940

CTAAGACTAC CATTCATAAA GAAACACAGT GGGAAGGAGT CTCAAGGAAG C TAGAAGTTG    3000

CACTACTAAT TTTGGTATTT TCAGAAACA ATGAAATTAA CTACAGTGTT A AGGATATTT    3060

ATTTGTGCAT AGTACTAAAA ATGCATTGAA AATGGGCTTT TCTTACTAG T AAAGAGTCA    3120

GTATTCTTC ATAAGTCTCA GAAGAGCTGA GAATTTTGTT GAATGTATTG T ACAGTATAT    3180

AGGAGCAAGA AAACTTTGTA AATTGGAAAG ATGTCTGTTT TTATAACTTA T TTTCATTTT    3240

TAAAGCTTAA ATGTAGATAT TTATATATAC AGGGTGTCTA GAAGCCAGTG T TGTTTCTTG    3300

CCATTACAGC TAACATAGTA AACAATAACT TTGACTTTCA AGTATGAAAT A GTTAAGTTA    3360

TAGCTGCAAA GAATACAATA TCTAANCTGT ATGTCACATC TACCTAAATA T TGCACTATA    3420

TGCTTAAAAT CATGTTGGTT TTAAAGTAGT TCTAAAATGT ACTAAATAAT A ATTTAATAT    3480

TTTCTTTTTA AATTATATTG GAGGGTCATA TAAATTAATC TGGTGAATTG T ATATGTGTT    3540

TGAAATTTTC ATTTTGTTTA AAAAAAAAAA AAAAAAAAAA AAAAAAAAAA A AAAAAAAAA    3600

AA                                                                   3602
```

(2) INFORMATION FOR SEQ ID NO:2:

(i) SEQUENCE CHARACTERISTICS:
        (A) LENGTH: 751 amino acids
        (B) TYPE: amino acid
        (C) STRANDEDNESS: single
        (D) TOPOLOGY: linear (xi) SEQUENCE DESCRIPTION: SEQ ID NO:2:

```
Met Ala Lys Arg Ser Arg Ser Glu Asp Glu A sp Asp Asp Leu Gln Tyr
1               5                   10                  15

Ala Asp His Asp Tyr Glu Val Pro Gln Gln L ys Gly Leu Lys Lys Leu
            20                  25                  30

Trp Asn Arg Val Lys Trp Thr Arg Asp Glu A sp Asp Lys Leu Lys Lys
        35                  40                  45

Leu Val Glu Gln His Gly Thr Asp Asp Trp T hr Leu Ile Ala Ser His
    50                  55                  60

Leu Gln Asn Arg Ser Asp Phe Gln Cys Gln H is Arg Trp Gln Lys Val
65                  70                  75                  80
```

-continued

```
Leu Asn Pro Glu Leu Ile Lys Gly Pro Trp Thr Lys Glu Glu Asp Gln
            85                  90                  95

Arg Val Ile Glu Leu Val Gln Lys Tyr Gly Pro Lys Arg Trp Ser Leu
            100                 105                 110

Ile Ala Lys His Leu Lys Gly Arg Ile Gly Lys Gln Cys Arg Glu Arg
            115                 120                 125

Trp His Asn His Leu Asn Pro Glu Val Lys Lys Ser Ser Trp Thr Glu
        130                 135                 140

Glu Glu Asp Arg Ile Ile Tyr Glu Ala His Lys Arg Leu Gly Asn Arg
145                 150                 155                 160

Trp Ala Glu Ile Ala Lys Leu Leu Pro Gly Arg Thr Asp Asn Ser Ile
                165                 170                 175

Lys Asn His Trp Asn Ser Thr Met Arg Arg Lys Val Glu Gln Glu Gly
            180                 185                 190

Tyr Leu Gln Asp Gly Ile Lys Ser Glu Arg Ser Ser Ser Lys Leu Gln
            195                 200                 205

His Lys Pro Cys Ala Thr Met Asp His Leu Gln Thr Gln Asn Gln Phe
        210                 215                 220

Tyr Ile Pro Val Gln Ile Pro Gly Tyr Gln Tyr Val Ser Pro Asp Gly
225                 230                 235                 240

Asn Cys Val Glu His Val Gln Thr Ser Ala Phe Ile Gln Gln Pro Phe
                245                 250                 255

Val Asp Glu Asp Pro Asp Lys Glu Lys Lys Ile Lys Glu Leu Glu Leu
            260                 265                 270

Leu Leu Met Ser Ala Glu Asn Glu Val Arg Arg Lys Arg Leu Pro Pro
            275                 280                 285

Gln Pro Gly Ser Phe Ser Ser Trp Ser Gly Ser Phe Leu Met Asp Asp
        290                 295                 300

Ser Met Ser Asn Thr Leu Asn Asn Leu Glu Glu His Thr Thr Glu Phe
305                 310                 315                 320

Tyr Ser Met Asp Glu Asn Gln Thr Val Ser Ala Gln Gln Asn Ser Pro
                325                 330                 335

Thr Lys Phe Leu Ala Val Glu Ala Asn Ala Val Leu Ser Ser Leu Gln
            340                 345                 350

Thr Ile Pro Glu Phe Ala Glu Thr Leu Glu Leu Ile Glu Ser Asp Pro
            355                 360                 365

Val Ala Trp Ser Asp Val Thr Ser Phe Asp Leu Ser Asp Ala Ala Ala
        370                 375                 380

Ser Pro Val Lys Ser Thr Pro Val Lys Leu Met Arg Ile Gln His Asn
385                 390                 395                 400

Glu Gly Ala Met Glu Cys Gln Phe Asn Val Ser Leu Val Leu Glu Gly
                405                 410                 415

Lys Lys Asn Ser Arg Asn Gly Gly Asp Ser Glu Ala Ile Pro Leu Thr
            420                 425                 430

Ser Pro Asn Val Val Lys Phe Ser Thr Pro Pro Thr Ile Leu Arg Lys
            435                 440                 445

Lys Lys Arg Ile Arg Val Gly Gln Ser Ala Gly Ser Glu Leu Gly Asp
        450                 455                 460

Gly Ser Leu Ser Glu Val Gly Asn Ala Ala Leu Lys His Thr Pro Val
465                 470                 475                 480

Lys Thr Leu Pro Phe Ser Pro Ser Gln Phe Phe Asn Thr Cys Pro Gly
                485                 490                 495

Asn Glu Gln Leu Asn Ile Glu Asn Pro Ser Phe Thr Ser Thr Pro Ile
```

```
                500              505              510
Cys Gly Gln Lys Val Leu Ile Thr Thr Pro L eu Gln Lys Glu Ala Thr
            515              520              525

Pro Lys Asp Gln Lys Glu Asn Val Gly Phe A rg Thr Pro Thr Ile Arg
    530              535              540

Arg Ser Ile Leu Gly Thr Thr Pro Arg Thr P ro Thr Pro Phe Lys Asn
545              550              555              560

Ala Leu Ala Ala Gln Glu Lys Lys Tyr Gly P ro Leu Lys Ile Val Ser
            565              570              575

Gln Pro Leu Ala Phe Leu Glu Glu Asp Ile A rg Glu Val Leu Lys Glu
        580              585              590

Glu Thr Gly Thr Asp Ile Phe Leu Lys Glu G lu Asp Glu Pro Ala Tyr
        595              600              605

Lys Ser Cys Lys Gln Glu His Ser Ala Ser V al Lys Lys Val Arg Lys
    610              615              620

Ser Leu Ala Leu Glu Ser Trp Asp Lys Glu G lu Pro Gly Thr Gln Leu
625              630              635              640

Leu Thr Glu Asp Ile Ser Asp Met Gln Ser G lu Asn Ile Leu Thr Thr
            645              650              655

Ser Leu Leu Met Ile Pro Leu Leu Glu Ile H is Asp Asn Arg Cys Asn
            660              665              670

Leu Thr Pro Glu Lys Gln Asp Ile Asn Ser A la Asn Lys Thr Tyr Thr
        675              680              685

Leu Asn Lys Lys Arg Pro Asn Pro Asn Pro C ys Lys Ala Val Lys Leu
        690              695              700

Glu Lys Ser Leu Gln Ser Asn Cys Glu Trp G lu Thr Val Val Tyr Gly
705              710              715              720

Lys Thr Glu Asp Gln Leu Ile Met Thr Glu G ln Ala Arg Arg Tyr Leu
            725              730              735

Ser Thr Tyr Thr Ala Thr Ser Ser Thr Ser A rg Ala Leu Ile Leu
            740              745              750
```

(2) INFORMATION FOR SEQ ID NO:3:

(i) SEQUENCE CHARACTERISTICS:
        (A) LENGTH: 5889 base pairs
        (B) TYPE: nucleic acid
        (C) STRANDEDNESS: single
        (D) TOPOLOGY: linear (xi) SEQUENCE DESCRIPTION: SEQ ID NO:3:

```
AAGCTTGACT AGTCTCATAG TTATCAGTAT TATAGTCACG AAAGGAATTA T GAAAACAAT    60

GTGAGAAAAT TATCAGCTTA GTTGTGCATT CTTTTTAAAA AATCAATGAT A TGAACAATT   120

GTTTGATTTT GGGATTGACT GAAACAGTGT AATAGAGGAA TTTGTACAAT A GTGACTTTA   180

GTTCTTCTCA AAACAAGTAC CAAGTATGAC TCAAGAGTAT GAGAATAGGG C TGGTGAGAT   240

GGCTCAGTGG GTAAGAGCAC CCGACTGCTC TTCCGAAGTC CAGAGTTCAA A TCCCAGCAA   300

CCACATGGTG CTCACAACCA TCCATAACGA GATCTGACTC CCTCTTCTGG A GTATCTGAA   360

GACAGCTACA GTGTACTTAC ATATAATCAA TAAATAAATC TTTAAAAAAA A AAGAGTATG   420

AGAATATCAT CTACATACCA GGGGTGGAGG AAATATTTCT AATTTTTATT C CTCTCAATA   480

GGATGACAAG TTAAAGAAGT TGGTTGAACA ACACGGAACT GATGATTGGA C TCTAATTGC   540

TAGTCATCTT CAAGTACGTG AAATGTCAAG TTGTATTTCT GTTACAACAT T TCTTTATTT   600

AAACCATTAG TTTATATATT CTATTTTTCA GAAATGTGTC TGTATAGTTT G GTTTTCATC   660
```

-continued

```
CTTAAAACAT CTGGTTAAAT TATTTTCTGG TATGTTTGTA GTTGTTTGTT A ATGGTTTAG      720
AAAGTAATTT TCCAATTCAG GCTGAGTACC TGAAATCCAA AAATTGGAAA T TTCTAAAGT      780
GCTTCAAAAT CTACAACTTT TTGAGTACTG ATTTAGAGCC ACAGTTTTAC A CTTGACTTA      840
ATGTAATACA TCACAGTAAA ATGCCAGGTA TGCCTGAAAT GTTACTATTA T TAGATTATG      900
TGTATAAGGT AGATATGAAA CATAGATGAG TTTCATCTAT AGACTTCTGT T CCATCCCCA      960
GGACATATTA TTTTATGCAT ATGTACATAT TTCCAGATCT CCAAACTGAA A TCTGAAACA     1020
ATTTTAGTCT CAAAAATTTT GGATAATGGC TGCTTAACTT GTAAAGCATT T TTCCAGGGG     1080
CCTAAAAGAA CTTTTACTAT AAAACAAAAT GGCATTAACT TTTGGTAGAA C TTCAAAAAT     1140
ATTTGTGACA AGTGGTTTTA TTTTATTTTG ATTTTTGTAT GTTGGTAATT G AACCTAGGG     1200
CCTTGTAAAC TCAGCCAAGC ACTTTACTAT TGATCTATGT CCTCAACTGT G ATATATGTG     1260
AAATTATTTT GAAGAACTTT ACTATTAAAA CATTTTGACA GCTAACAAAT A AAATCAAGA     1320
AAAAATTGTT AGGTTTCTTA TCTAATGCAT ATGTTTTTGG GTATTTTTAT T GATTTTTTT     1380
TTTTGAGATG AAGTCTTACA TAGTACTTAC TTACTTACTC GGGTAGCCTG G AAGTCATTA     1440
TGTAAATCAG GCTGGCCTCA AACTCATAGA TATCTGCTTA CCTCTTTCTC C TGAGTGATA     1500
GGGTAAAGT TGTAAAGTAT CATACCTAGC TATTTACATT TTTATTATTT T ACAGTATAC     1560
TTGTTCATCA TACCAATATC GCATATTATT GGCATATAAT TTTATATGCA A TATGAAGTA     1620
CTTCTGCATG TACTCATTTG TTTCTTAAGA GCATTGTGAG TTGTTAGATA A ATTACCTAA     1680
ATTTTAAATT TCAGTGTTGA TTCTTTTTGG TTTCAGAAAC AAGGTTACCT T TGGGTTTTT     1740
GTTTGTTTAT TTGTTTTCAT ATAACATAGA ACTCTCAGTG TAACATGAAA A CTGAGAATG     1800
AAATAATGGG AGAAAACAAA TTATAGAGTT AGTGCAAATT ATATTCAAAT G TCAGCTCTG     1860
TTAATTTAGA GAAAATACTT CTTTGGCCTT CCGCTACTTG CTTCTATAGT A TTGTGAGAA     1920
TTACAAATAT AAACAAGGTT GGCACAGTTC CTGACATTTA GCATTAGTC A GTAAAAGCA     1980
AACTCAAGGG CTGGAGAGAT GGCTCAGCAG TTAAGAGCAC TGACTGCTCT T CTAAAGATC     2040
CTGAGTTCAA ATCCCAGCAT CACATGGTGG CTCACAACCA TCCATAATGA G ATCTGATGC     2100
CCTCTTCTGG GGTGTCTGAA GACAGCTACA GTGTACTTAC ATATAATAAA T AAATAAATC     2160
TTTAAAAAAA GCAAACAATT AGAAGTTAGT ATACTAGATT TAAACTAGAG G TTAAAATTT     2220
ATTTTATTTA TATAAGTACA CTGTAGCTGT CTTCAGATAC ACCAGAAGAG G GCTTTAGAT     2280
CCCATTACAG ATGGTTGTGA GCACCATGTG GTTGATGGGA ATTGAACTCA G GACCTCTGG     2340
AAGAACAGTC AGAGCTCTTA ACCACTGAGC CATCTCTCCA ACCCCCTCCC C TCACCCCCA     2400
GTTAATTCCT TTTTTTTTTT TTGGTTTTTC GAGACAGGGT TTCTCTGTGT A TCCCTGGCT     2460
GTCCTGGAAT TCACTCTGTA GACCAGGCTG GCCTCGAACT CAGAAATTCT C CTGCCTCTG     2520
CCTCCCAAGT GCTAGGACTA TGAAAGAATG CGCCACTACG CCTGGCCCCC A GTTCATTTT     2580
TTAAAGTGAC AATTTTTAAT CTACTTAATT GAAGTATTAA GTATATCTTC T ATGAAAGTG     2640
TTTCATGTTT TGTTGGTAAT TTGAAAGGAT AATTTATAAA TATACTTTCA C TACCACATA     2700
GAGACTAGTG ATGCCTTAGA TGCTGTACAA ATTGAGCGCT ATGCTTAAAT C TTATATCTG     2760
CTTCATATAG TTTAATCCTG TCATTTATTT CTCAATTCTG GATTAATTTT T TATGGACTA     2820
TGTCTTGCTG CTTGCTGTAT TATAAGGATA GTATAGAGGT ACATGTCTTA A TTTCAAATA     2880
TGTTGTTTTT AATTTGTAGC CTAAACCTAT GATTAATTGA AAGAGCAGAA T TGGGATTTT     2940
AGGCATGTAA AATAAGCATT GCATATAATA GTTTGATATT GAATATTTTT T TGACTAATA     3000
```

```
TTTGTTCATA TGGGTATACT TAAATTTGGG CTAATTTACT TCCTGGAGAT A TATAGTCAA    3060

CAATAAAATT GTCCAAATTT TTTCAGAATC GTTCTGATTT TCAGTGCCAA C ATCGATGGC    3120

AGAAGGTTTT AAATCCAGAA TTGATAAAGG GTCCTTGGAC TAAGGAAGAA G ATCAGAGGG    3180

TAATATATTC ATATTCTTTT GAAAAAATTT ATTATTTATT TGTGTATATA T GTTTGGGGA    3240

CATGTATGTG TGTTTATCCT TATGCCACAG CTCACATGTA GAGGTCAAAG G ATAATTTGT    3300

GGGAACTAGT TCTCTCCTTC CACCCACTGG TGGTCTTAGA GATCAAACTT G GTCATCAGG    3360

TTTAATGCCA AGTGCCATGG AGCCATTCCT TGCTCCTTGT TCATATTCTT T ATGTTCACT    3420

GTACTGATGG ATTAGATTAA TTTTCTTATT AACATGGTTT AACACAAAGT A TGATATGTG    3480

TGTGTGTGTG TGTGTGTATG CTAAGGTTGG AGGTGGACAT ACATGTATTG C AAACATATG    3540

TGAGGAGGCT GGAGGACTGG TGGTGTTTCT TAAGACAGTA TCATTCGGGA T TTATTTTTA    3600

TGACATGGGG GCTCTCATTG GTCTTAAGGT TGCCAAGTAG GAGTAGGTTG G TGGGCCTGT    3660

GAGCATTATG GATCTGCCCC ATTGCTGGGA TTGCATGTAT ATCCATTATG C CTGGCTTTT    3720

AAAAATGTTG TTTCTGGGTA TGGAATTCAG GTTTTCATGC TTCAAGGAAA G CACTTCAGT    3780

AACTGAACCA TTTCCCCAGT GCACACTTTA AGTTTGTTGG TTCTGTTCTT T GGAGGCTAT    3840

AAGCATAAGA ATTGAATGTT GAATGCCTTG AAATGTAGCT TTTTCTCTCC T AGGGCAAGG    3900

ATAAGTGAGA CAATTTATAA TAAGTACTGT CCTTTTTGAG AGCTTCATTT A CAAAAGGAA    3960

AAATACTTTA AAGTTTGGCT TAGCAACATG TCAGGCATAG TTTCCTATCA A AATTTAATT    4020

AACATTAAAA ATAAATTTTA ATTTTATTTT CATATTTAAT AACTTGATAT A TTAGGAAAT    4080

CACTCTTAAT TTTTCCTCTT GACCGTAATG AATCTCACGA TTAGACAAGT A TCAGGACAT    4140

CATGTTTCCA GAGGGGTTGT AATAAAAACC AATTATTTGT GCAATAAAAG T TGTTGAAGA    4200

ATAGAAGCAT CTGCTCTCTA CTAGGAATTG CTCTTTAATT CTTACCCTTA G CTTTCCTGT    4260

TGCTAAGGTG CCTGTGGAAT TAGGACATCC TTATACCCAT AAGAGCAAAC A AACAAAAGT    4320

TACTTCATGT GGCTCAGGAC TGATCTGACT TTTCTTAATG GGCGATGATA A GTTTTGAAA    4380

ATGTGATCTG GGGCTAGTGA AGAGGACAGT TGTCTTCTGT CTTCTACATA G TCACTGTGG    4440

TTTGTATTTG TCTAACACTC ATACTTACAA ATCATAAACA TGAAATAATA A TAATAAAAA    4500

TGATTAAGTA AAATACAATG TGAGCTCTGT TAAAAAGATA TTTAATGGCT G GATCTAGTA    4560

CATTGTCTAT AATTCTAGCT ACTCAGTAGG TCTAGATAGG ACATTCATGG C AAGTTTAAG    4620

GCCTACCTGG GTAACTTAGT GAGACCCTGT TTAAAAATCG AAATGAAGAA A AGGGCTGGG    4680

AATATAATTC ATGGTAGAAC ACTTGTTAAA CATACCTAGT ACTGGGAAA A AAGAAAAAC    4740

CAAAAGCTG TAATCAAATA ATCAAAGCTG TACATTTAAC CTTTAAGTCT T ATTTTTTAA    4800

AAATATGACA AGTAGACACA TTTCAAGAAA ATTGTGATAG ATGTTAAACT T AATTAATCT    4860

ACCAATACAG AGTGAGCATA ATTCTTTGTG ATTCATGTGA TACTTGACTG G GTCAGGTAG    4920

CAGGGCAAGT AGGTGGGCCA AGGAGATGAA CTGTTCTTTA AATTTTAGTT A AACTAAAAG    4980

GCAAAGCAAA ATATAGGACA AATGTACAAA TGTTACTTCA GTTACTTCAA A TTACTTCAG    5040

AATAATATCT ATGAGTAATT AGCCCCTTGA ACTTTTGAT GCATTTGGG T ATTGATTTT     5100

TGAACTCGTT GAGTGCTGAA GGATAGCTAT TATTAACATT ACCTTCTGTG A ATTATAGTT    5160

ATAGCTGAAA TTTAATCCAT GTTTTCTTTT TTTGGTCTTT TGAGACAGGG T TTCTCTGTG    5220

TAGCCTTGGC TGTCCTGGAA CTCACTCTGT AGACCAGGCT GGCCACCACG C CTTAAGTAG    5280

AATTCTTAAT TTGGAGTTTT TTTTCTCTTT TTGTTGTTGT TGTTGAGGTG C TTCAGATCA    5340

AACCTAGGAC CTTGTATTGG GAATAAAAGA AAAACCAAAA TGTTCCGTAA T GACCCCAAC    5400
```

-continued

```
CTTGACTTGT TTGAGTTACA TTTTAAAATT CTTTCATAGT AATAGTTTTT C AATCTTTGA      5460
TTTTGCTTCT TAGGTTATTG AATTAGTTCA GAAATATGGG CCAAAAAGGT G GTCTTTAAT      5520
TGCAAAACAT TTAAAAGGAA GAATAGGCAA GCAGTGCAGA GAAAGATGGC A CAATCACCT      5580
GAACCCTGAA GTGAAGAAGT CTTCCTGGAC AGAAGAAGAA GACAGGATCA T ATATGAAGC      5640
ACACAAGCGC CTGGGAAACC GTTGGGCCGA GATTGCTAAG TTACTTCCTG G AAGGTGCTT      5700
ACATAAATAA GTTTCTGTGC TTCAACATGA CCTTGACTAC CTTACTATTG A ATATATTTT      5760
CAAGTATTTC CTTTCTATTA TTCACAATTC AAGTTTAGTC TGCATGCTAT G AGCAACCAT      5820
TTGGGTACAT TTGTAATTTT GTGGTAAAGA ATATAATTTG TACAATAAAA T GGTAAAACC      5880
TTTAAGCTT                                                               5889
```

(2) INFORMATION FOR SEQ ID NO:4:

(i) SEQUENCE CHARACTERISTICS:
        (A) LENGTH: 6775 base pairs
        (B) TYPE: nucleic acid
        (C) STRANDEDNESS: single
        (D) TOPOLOGY: linear (xi) SEQUENCE DESCRIPTION: SEQ ID NO:4:

```
AAGCTTGATA GAAGCATTAA CTGTCCAAAC CATTCGTAGC TGTTGAGGCA C AAAAAGAAA        60
GCTGTCCCTT CTTAGGTTTA TGTTTGTTTA TTTTTTTCAG ACAGAGTCTC A TGCTGTAGC       120
TCAGGCTACT GTAGCTCAGG CTGCCTTCGA GTTCATTATG TAGTTTAGCA G GGCCTTCGA       180
AACTCACAGC AGTCCCCTGG CTCAGCTGGG ATCAGAAGCC TGTGACCACC C ACCATCCTG       240
GCTTATGTTT GGTTTATGAT AGACACATAC CAGGTTTAGC CTGTAGTGTA G TGTTAGTGG       300
AAGCCAGAAG AGGGCATCAG ATCGCCTGGT ACTGGAGTTG CAGTCCATTG T GAGCTGCTA       360
TGTGGGCTGG GAATTGAAAC CTGGAAAAGC TCTTAACCAC TGAGCCATCT T TCCAGCTCC       420
AGCTTTTTTA AATTAAAAAT GAAGCAATTA TAAATGCTTT CCAAAGTGCC T AACCCACCT       480
GCATTCCTAT GAGCAAGCAG GGAAGTTCTA TATGCTTCAG TATTTTTATT T TTAGCTCTT       540
TCTTTTTTAG ATACCTCACT ACTACTAAGT GTATGCATTT TTACCATATA T TGTCAGACA       600
AGGTCTCATT GTATAACTCA GGAGACTCAG AACTCATAAG CCTTTTGCCT C AGCGTTTTT       660
AGTTTGGGGG TTACATTTCT TGCTTCTTTG TGGTTGAAAA TCGTGTAAGT G AGAGATTGT       720
TACATGTGTT TCGTTACTTT TCTTTCTTCT CCCCTTCCCC CCACCCCACT T TCTTTTTGA       780
GACAGAGTTT CAATTTAGCT CGAGCTGGGC TGGAATTGAA CTCCCAACTG C TGGATACTA       840
CTGGATTACA ATGTAAACCA CCACATTCAG CTCGCTTTTA TATCTTTTGT T TTTGGCAAA       900
GTAGTCATCT TTTGTAGACT TTAATTGTTT TTATTCCTCT CATTGAATTT T GAGAGTGTA       960
AAACCTCTCT GAATGTTATA TTGTGTGTAT GTGAGTTCAT GTGAGCATGC A TATATGCTA      1020
CACTTCAAAT ATGGAGGTCA GAGTATAAAA ACATTGGGTG TTGATCCTTG C CTTCTACTC      1080
TGTAAGACTG TAAAAGTACT GGGCTTTTCT ATGCTTGCTC TTGTTCTGAA A TAATGACAC      1140
AGGGACCTGG TATATTTATT AATAAGTTTC AAGTACTACA GCTGAGTATA T ATCCATCTA      1200
TTCTAACCGA CTGTGCTGCC TACTACACAG CCACATGACC CATTACTTGC C ATTTTAGGC      1260
TCTCCTGGCT GCTCCTCTCC ATCTGTGTCC ACAAGGTCAT TCTCTTGTCT G GATACCTCC      1320
ACCTGGGACT CCCTCAATGG GATTGGAAGT CCTACCTTCA CTCTCCTCCC A ATTATAGCC      1380
CGATCAGCTC TTCATCAACC AATCAGAAGT GGCGGGGAAC AATACACAGG A AATGCTTCA      1440
ATAATAATGA CAATGCTAAC TCTCAGATCT CAGGGCACAG TAGCAGCATC T GAATACACA      1500
```

```
GCATACAAAA CTCTCCCCCA GAGTCTTGTT CAGCACTACA TAAAGCAGTC C AGCTGGCCA      1560

GAGAACTTCA AGTGTTCTTC TTTATCTGCC ATCATCTGCT GTAGGCGCTC T GGAGATCTG      1620

GTCAGCCTTG AGTACATAAC ACCACCTTGT CTCAAAGTAT TCTGTAATAC T ATCTTTGGG      1680

AGGACGTTTC CCTATATAAA ACAATGAGAA TAAATTTTAC TTAAAAATCT G ATGCACTTA      1740

CCTTCAAGTT CTAAAACGGT TGTTTGTATA AAGCTGATCA TAACCTAAGA A TATCAGTTT      1800

TGCCTTCCTG TTAGAATAAA AATGAACAA TGCATACCCA AGAGTAAATA T GCTTCCAAA       1860

TGACATTTGA AGACTAGGAG GAGCATTCCA TCATGTAGCC CTGGTGAAGC T AAGGTAGAT     1920

CATGAAGAAA GTCTGGGCTC TATCTGAGTT CAAGATCAGC CTGGGGTACA T AACAACACC     1980

TTGTCTCAAA AATATTAATT TCTAAATTAG TCTCTCTCTT TAGAAGCTAC T ATGGAACTC     2040

AGAAAATAAT TTAAAAGTGC TTTTCCTTCC CAAAATATAT CTTGAGAAAA A GGAAGTTAT     2100

TTTTTTTTTA AAAGCGAGTG TGTATCTACC TGGTTGTTTT GAATTGCAAG C TCATCTTGA     2160

TTTGTATTTG CACCTGTATC TCTGATTTGC AAAAGACGAT GCGTACAGTT T CAAAATAGC    2220

AAAAAATGTC AGTTTGTAAC AACATTGATC TGTGGTTCAT CACTCTATGC A GTAGAGCAT    2280

GGTGTCTTGC AAATTTGGGC TCTTCGCCGT GTCTAATCGC TACTGTAGTT A ATAATCTCC    2340

TTGTATGCTT CTTTAACCGT GTAACTGTTG AGAAGCTGCA ACTGTAAGAG G CCCCTTCCC    2400

CTATGCAAGA TTTCAGTTAC TCCAGCTTTC AGGCGCACCT CCGGGACTCT G GGTTCCCTG    2460

CGCAGAGCAT CCCGCCCCCT TTGTAGATGG AGTAGGAGGT TGAGCTTCTG G AGCACTATC    2520

AACCTTTTCC CGTTCCACGC AAGCCTCGAG ATAACAACTC CCCACTTATC A CACTTTTAT    2580

TCATCTCTGG GGAAAACAAA AGACACAACA ACAGGGTCTT GGCCAGTTTC C TTGTCCTTT    2640

CGGCGCAGAA CTAACTCACA CATGCTTAAG AAAATAACGG CCGCGCAAGT T TCCTGGCTA    2700

GAAGGTTAAG TAGATGACCG CGCCCTTAAG TGGCGAGACT CACAGCGCGA A CTAGCGCCC    2760

GCGAGGTCCT CCCCTGCTCA GGACCCCGAC TGTCCCCGCC CCAGAGGCAC G CTCCGCACC    2820

CCTCGGAGGT GGNNNNGTGG ATCGGCCCCT NNNNCCTCTT CCGGCACACA C CCNNNNNNN    2880

NNNNNNNNNN NNNNNNNNNN NNNNNNNNNN NNNNNNNNNN NNNTCGGGA C TCCCGCGAG     2940

TTCCAATCCT GCTTCTAGCC CCGCCGGCCC GCCCTCTGCC GCGCCGGCCC T CGCCGCCCC    3000

GCCCCCGCCC CCCTGCGCGC GGCCGCCCCA GCCAATGAGG TTCGGGGCCC G TGCGCAGAT    3060

TCAAACGGCG GCTCTTGAGG GAGGCTGGGC GCGAGATTCG GCGGTGCGGA C AAAACCCTG    3120

CAGGAGGCTG CGAGTGCTGC AGTGCTGCTC GCTGCGGGGA GAGGGCGGGG G TCGGCGCCG    3180

TGACGGAGCG GCCGAGGGCC GGCAGCTCTG AGGCGGAGGC GGCGGCGGCG G GCGGGGCGG   3240

CGGCGGGCGG GAGCACGCCT CCTGACATGT CCAGGGCATC CCTGGCCGGG C CCGCCGCGG   3300

CTAGGAGCAG TGGGTCTTGG TCCGCCCCTC TGTCCCTCAG TCCCGCCTGG C CCTGACCTG    3360

ACCGGGCCTG CTTTCCGCTC TCGGTCACCT GAGGGAAGGA GTTGGGGAAG C GGCGGGTGG    3420

GTCTCGGAGA GGGAGCATTG GCCCCAGGCT GGAGGAGGCT GACCCCGCGT C CCCGCCCAG    3480

CCCGCGCCTA TGCGGTACTT GAAGGATGGC GAAGAGGTCG CGCAGTGAGG A CGAGGATGA    3540

TGACCTTCAA TATGCTGATC ATGATTATGA AGTACCTCAA CAAAAAGGAC T GAAAAAACT    3600

CTGGAACAGA GTAAAATGGA CAAGAGATGA GGATGACAAG TTAAAGAAGT T GGTTGAACA    3660

ACACGGAACT GATGATTGGA CTCTAATTGC TAGTCATCTT CAAAATCGTT C TGATTTTCA    3720

GTGCCAACAT CGATGGCAGA AGGTTTTAAA TCCAGAATTG ATAAAGGGTC C TTGGACTAA    3780

GGAAGAAGAT CAGAGGGTTA TTGAATTAGT TCAGAAATAT GGGCCAAAAA G GTGGTCTTT    3840
```

```
AATTGCAAAA CATTTAAAAG GAAGAATAGG CAAGCAGTGC AGAGAAAGAT G GCACAATCA       3900

CCTGAACCCT GAAGTGAAGA AGTCTTCCTG GACAGAAGAA GAAGACAGGA T CATATATGA       3960

AGCACACAAG CGCCTGGGAA ACCGTTGGGC CGAGATTGCT AAGTTACTTC C TGGAAGGAC       4020

TGATAATTCT ATCAAAAATC ATTGGAATTC TACCATGCGA AGAAAAGTGG A ACAGGAGGG       4080

CTATTTACAA GATGGAATAA AATCAGAGCG GTCTTCATCA AAACTTCAAC A CAAACCTTG       4140

TGCGACTATG GACCATTTGC AAACCCAGAA TCAGTTTTAC ATTCCTGTTC A GATCCCTGG       4200

GTATCAGTAT GTGTCGCCTG ATGGCAATTG TGTTGAACAT GTTCAGACAT C TGCCTTTAT       4260

TCAGCAACCC TTTGTTGATG AAGATCCTGA TAAAGAAAAA AAAATAAAGG A GCTCGAGTT       4320

GCTTCTTATG TCAGCCGAGA ATGAAGTTAG AAGGAAGAGG CTTCCACCTC A ACCTGGAAG       4380

CTTTTCTAGC TGGTCTGGTA GTTTCCTCAT GGATGATAGT ATGTCTAACA C ACTGAATAA       4440

TCTGGAGGAA CACACTACTG AGTTTTATAG CATGGATGAA AATCAAACTG T TTCTGCTCA       4500

GCAGAATTCA CCCACAAAGT TTCTAGCTGT AGAAGCAAAT GCTGTGCTGT C TTCTCTACA       4560

GACCATCCCA GAATTCGCAG AAACTCTGGA ATTAATTGAA TCGGATCCTG T AGCATGGAG       4620

TGATGTTACC AGTTTTGATC TTTCTGATGC TGCTGCTTCT CCTGTCAAGT C TACTCCAGT       4680

TAAATTAATG AGAATTCAAC ATAATGAAGG AGCCATGGAA TGCCAGTTTA A CGTCAGTCT       4740

TGTACTTGAA GGGAAAAAGA ACAGTCGTAA TGGTGGAGAC AGTGAAGCTA T TCCTTTAAC       4800

ATCCCCAAAT GTGGTCAAGT TTAGCACTCC TCCAACCATC CTCAGAAAGA A GAAAAGAAT       4860

TCGAGTGGGT CAGTCTGCAG GCAGTGAGCT TGGCGATGGC TCACTTAGCG A AGTTGGTAA       4920

TGCAGCACTC AAACACACAC CAGTGAAAAC ACTACCATTT TCTCCTTCTC A GTTTTTTAA       4980

CACATGTCCT GGAAATGAAC AACTTAATAT AGAAAACCCT TCCTTTACAT C AACCCCAAT       5040

TTGTGGGCAG AAAGTTCTCA TTACAACTCC TCTTCAGAAG GAAGCAACCC C CAAAGATCA       5100

AAAAGAAAAT GTAGGATTCA GAACTCCTAC TATTAGAAGA TCTATACTGG G CACCACACC       5160

AAGAACTCCT ACTCCTTTTA AGAATGCACT TGCTGCTCAG AAAAAAAAAT A TGGACCTCT       5220

TAAAATTGTG TCCCAGCCAC TTGCCTTTTT GGAAGAAGAC ATTCGAGAAG T TTTAAAAGA       5280

AGAAACTGGA ACAGATATAT TCCTCAAAGA GGAAGATGAA CCTGCTTATA A AAGCTGCAA       5340

ACAGGAGCAC TCTGCATCTG TGAAGAAGGT CAGAAAATCC CTTGCCTTAG A GAGCTGGGA       5400

CAAAGAAGAA CCAGGGACTC AACTGCTAAC TGAAGACATT TCAGACATGC A GTCAGAAAA       5460

TATTCTTACA ACATCTTTAT TAATGATACC ATTATTGGAA ATACATGACA A TAGGTGCAA       5520

CTTGACTCCT GAAAACAAG ATATAAATTC AGCCAACAAA ACATATACAC T TAATAAAAA       5580

GAGACCAAAC CCTAACCCTT GTAAAGCTGT CAAATTGGAA AAGAGTCTTC A GTCAAATTG       5640

TGAATGGGAA ACAGTGGTAT ATGGGAAGAC AGAAGACCAA CTTATCATGA C TGAACAAGC       5700

GAGAAGATAT CTGAGTACTT ACACAGCTAC CAGCAGCACA TCAAGAGCTC T AATACTCTA       5760

ACTGTTACTA AAGCTGATAA AATGCCCTAC CCCTTTACTG TATTTTATGC T AAATTAGGT       5820

TGCAATGAAA TTTGTCTCAA TTAATTCTTT TAAAGGTTTT AATACATCCC T AAAATGGTT       5880

CACGTTTTTT TCTATATTGA ACAGGCAAAA AACTAATAAG CTACTTAAAG T AAGGGGTAG       5940

GCAAATTTAT TATTTATATG TTTAAGAAAT GAGAGTTTTA AAATTTGTTT T AAAGAACAA       6000

AATGGGAAAA TAAGCATGTT TCTGGATATT CCATAGTAAA TTCTCACATA A TTTCTTTAC       6060

AGGATATATG TTGCTACTGT CTCAAGGCTG TAGTCTGTTA TAAACAAGTT A AGTATGTGT       6120

GACCTCTGAA AGTCTATCTG AGTACTTACA CAGCTACCAG TAGGGGGATC C TCTAGAGTC       6180

ATCCATCACA CTGGCGGCCG CTCGAGCATG CATCTAGAGG GCCCTATTCT A TAGTGTCAC       6240
```

-continued

```
CTAAATGCTA GAGCTCGCTG ATCAGCCTCG ACTGTGCCTT CTAGTTGCCA G CCATCTGTT    6300

GTTTGCCCCT CCCCCGTGCC TTCCTTGACC CTGGAAGGTG CCACTCCCAC T GTCCTTTCC    6360

TAATAAAATG AGGAAATTGC ATCGCATTGT CTGAGTAGGT GTCATTCTAT T CTGGGGGGT    6420

GGGGTGGGGC AGGACAGCAA GGGGGAGGAT TGGGAAGACA ATAGCAGGCA T GCTGGGGAT    6480

GCGGTGGGCT CTATGGCTTC TGAGGCGGAA AGAACCAGCT GGGGCTCTAG G GGGTATCCC    6540

CACGCGCCCT GTAGCGGCGC ATTAAGCGCG GCGGGTGTGG TGGTTACGCG C AGCGTGACC    6600

GCTACACTTG CCAGCGCCCT AGCGCCCGCT CCTTTCGCTT TCTTCCCTTC C TTTCTCGCC    6660

ACGTTCGCCG GCTTTCCCCG TCAAGCTCTA AATCGGGGCA TCCCTTTAGG G TTCCGATTT    6720

AGTGCTTTAC GGCACCTCGA CCCCAAAAAA CTTGATTAGG GTGATGGTTC A CGTA       6775
```

(2) INFORMATION FOR SEQ ID NO:5:

(i) SEQUENCE CHARACTERISTICS:
        (A) LENGTH: 4880 base pairs
        (B) TYPE: nucleic acid
        (C) STRANDEDNESS: single
        (D) TOPOLOGY: linear (xi) SEQUENCE DESCRIPTION: SEQ ID NO:5:

```
GGAGGGACAG CGGCTAGAGG ATCGGGGAGA AGGAGCATTC GCCGGAGGCT G GAGGAGGCT      60

GACCCGCGTC CCCGCCCAGC CTGCTCCTAT GCGGTACTTG AAGGATGGCG A AGAGGTCGC     120

GCAGTGAGGA TGAGGATGAT GACCTTCAGT ATGCCGATCA TGATTATGAA G TACCACAAC     180

AAAAAGGACT GAAGAAACTC TGGAACAGAG TAAAATGGAC AAGGGACGAG G ATGATAAAT     240

TAAAGAAGTT GGTTGAACAA CATGGAACTG ATGATTGGAC TCTAATTGCT A GTCATCTTC     300

AAAATCGCTC TGATTTTCAG TGCCAGCATC GATGGCAGAA AGTTTTAAAT C CTGAATTGA     360

TAAAGGGTCC TTGGACTAAA GAAGAAGATC AGAGGGTTAT TGAATTAGTT C AGAAATATG     420

GGCCAAAAAG ATGGTCTTTA ATTGCAAAAC ATTTAAAAGG AAGAATAGGC A AGCAGTGTA     480

GAGAAAGATG GCATAATCAT CTGAATCCTG AGGTAAAGAA ATCTTCCTGG A CAGAAGAGG     540

AGGACAGGAT CATCTATGAA GCACATAAGC GGTTGGGAAA TCGTTGGGCA G AAATTGCCA     600

AACTACTTCC AGGAAGGACT GATAATTCTA TCAAAAATCA TTGGAATTCT A CTATGCGAA     660

GAAAAGTGGA ACAGGAGGGC TATTTACAAG ATGGAATAAA ATCAGAACGA T CTTCATCTA     720

AACTTCAACA CAAACCTTGT GCAGCTATGG ATCATATGCA AACCCAGAAT C AGTTTTACA     780

TACCTGTTCA GATCCCTGGG TATCAGTATG TGTCACCTGA AGGCAATTGT A TAGAACATG     840

TTCAGCCTAC TTCTGCCTTT ATTCAGCAAC CCTTCATTGA TGAAGATCCT G ATAAGGAAA     900

AGAAAATAAA GGAACTTGAG ATGCTTCTTA TGTCAGCTGA GAATGAAGTT A AAGAAAGC     960

GAATTCCATC ACAGCCTGGA AGTTTTCTA GCTGGTCTGG TAGTTTCCTC A TGGATGATA    1020

ACATGTCTAA TACTCTAAAT AGCCTTGACG AGCACACTAG TGAGTTTTAC A GTATGGATG    1080

AAAATCAGCC TGTGTCTGCT CAGCAGAATT CACCCACAAA GTTCCTGGCC G TGGAGGCAA    1140

ACGCTGTGTT ATCCTCTTTG CAGACCATCC AGAATTTGC AGAGACTCTA G AACTTATTG     1200

AATCTGATCC TGTAGCATGG AGTGACGTTA CCAGTTTTGA TATTTCTGAT G CTGCTGCTT    1260

CTCCTATCAA ATCCACCCCA GTTAAATTAA TGAGAATTCA GCACAATGAA G GAGCCATGG    1320

AATGCCAATT TAACGTCAGT CTTGTACTTG AAGGGAAAAA AAACACTTGT A TGGTGGCA     1380

ACAGTGAAGC TGTTCCTTTA ACATCCCCAA ATATAGCCAA GTTTAGCACT C CACCAGCCA    1440

TCCTCAGAAA GAAGAGAAAA ATGCGAGTGG GTCATTCCCC AGGCAGCGAA C TTAGGGATG    1500
```

```
GCTCATTGAA CGATGGTGGT AATATGGCGC TAAAACATAC ACCACTGAAA A CACTACCAT    1560

TTTCTCCTTC ACAGTTTTTC AACACATGTC CTGGTAATGA ACAACTTAAT A TAGAAAATC    1620

CTTCATTTAC ATCAACCCCT ATTTGTGGGC AGAAAGCTCT CATTACAACT C CTCTTCATA    1680

AGGAAACAAC TCCCAAAGAT CAAAAGGAAA ATGTAGGGTT TAGAACACCT A CTATTAGAA    1740

GATCTATACT GGGTACCACA CCAAGAACTC CTACTCCTTT TAAGAATGCG C TTGCTGCTC    1800

AGGAGAAAAA ATATGGACCT CTTAAAATTG TGTCCCAGCC ACTTGCTTTC T TGGAAGAAG    1860

ATATTCGGGA AGTTTTAAAA GAAGAAACTG GAACAGACCT ATTCCTCAAA G AGGAAGATG    1920

AACCTGCTTA CAAAAGCTGC AAACAAGAGA ATACCGCTTC TGGGAAGAAA G TCAGAAAAT    1980

CACTAGTCTT AGATAATTGG GAAAAGAAG AATCAGGCAC TCAACTGTTG A CTGAAGACA    2040

TTTCAGACAT GCAGTCAGAA AATAGATTTA CTACATCCTT ATTAATGATA C CATTATTGG    2100

AAATACATGA CAATAGGTGC AACTTGATTC CTGAAAAACA AGATATAAAT T CAACCAACA    2160

AAACATATAC ACTTACTAAA AGAAACCAA ACCCTAACAC TTCCAAAGTT G TCAAATTGG    2220

AAAAGAATCT TCAGTCAAAT TGTGAATGGG AAACAGTGGT TTATGGGAAG A CAGAAGACC    2280

AACTTATTAT GACTGAACAA GCAAGAAGAT ATCTGAGTAC TTACACAGCT A CCAGTAGTA    2340

CTTCAAGAGC TCTCATACTG TAATTGTTAT TAAAATTGAT GAAATGCCCC A CTCCCTTAC    2400

TGCAGTCTCT ACTAAATTAG GTTGCAGTGA AATTTTCTC AATTAGTTGT T TTTAAAGTT    2460

GTAAGATACC CTTTTAATAC AGCATCTTTT TTCTATTCTA TATAGTAGGC A GAAAGCTAG    2520

TAAGTCACTT AAGGGGTAGA TAGTTTCATA GTTTATTTTT TAAGAGATGA G ATTTTTAAA    2580

AATTGTTTTT AAAGAACAAG ATGGGAAAAT AATAGAATGT TCATGGATTT C TAAAAGTAA    2640

ATTCTCATAT ATTTTCTTCA CAAGATATAT GTTGCTACTC TCTTGATGCT G CAGTTTTGT    2700

TATAGATAGG TGTATGAGTA TATATGATTT CTGAAATTAG TCTATGTATG G AAAGCACAC    2760

ATGATTTTAT GAAGGTACTT TTGCCCATGT GCTGATTTAC TTAGGCTACC A TTTACAAAG    2820

AAACACATTG AAAAGGAATT TAAAGGAAGG ATAGAAAGTT GCACTACTAA T TTTTTGTTT    2880

TTTTTTTCAG AAGCAGTAAA ATTAACTACA GTGTTAAATG TATTTATTTG A GCATAGTAC    2940

TGAAAACAAA AAGCATTCAA AAAAGAGTTT TTTCTTTATT AGTAAATAGT A TTTTCTTAA    3000

TCTCAGAGGA GCTGAGAGTT TTGTTGAATG TATTGTACAG TATGTAGGAG C AGGAGAACT    3060

TTGTAAATTG GAAAGAAGTC TGTTTTTATA ATTTATTTTT ATTTTTAAAG C TTAAATGTA    3120

GATATTTATA GTATACAGGG AGCCTAGAAG CCAATGTTGT TTCCTGTTAT T ACAGCTAAC    3180

ACAGTAAAGA ATAATTTTGA CTTTAAGTAT GAAACAGTAG TAAGTTATAG C TGCAAAGAA    3240

TACAATATCT ATACTGTATG TCACATCTAC CTAAATGTTG CACTATGCCC T TTAAATCAT    3300

GCTGGTTATA AAGTAGTTCT AAAAATGTAC TAAATAATAA TTTAATATTT T CTTTTTAAA    3360

TTATATCGGG GGTGGTCATA TACATTAATC TGGTGATTTG TATATGTGTT T GAAATTTTT    3420

TGCTTTTGTT TAAAAAAAAA TAATATGGTA CCTTGGTCCC TAAAAACAGT C TGCACTTAG    3480

AAGTTATATT TACTCAGTGT TTCAGAAGTG GAGAACTTAT CTTTTATTTA T AAAAATATT    3540

TTGTCCTTTT TTAAATGTTT TGTGTTTCTC TACAGGTTAC AACAGTTGCT T CAGTTGCCT    3600

GTTTTAGGTG TTTGCACTTA TTTTATTTCT TCTTGAAAGA ATTTTTATTT G CTTTTGTGG    3660

TAGAGATTAT ATGTAATTTT TTTTCAGTCA TATAATGGTG TGCTGTCAAC T TAAACACTG    3720

ACAGGTAAAT AGAATTGTAC ACTGTAGTTT GAATTATTTA TAATTGACAC A CTCTCTCCC    3780

TCTCCACTCC TGAAGTATGC TGCTATAGAA AATAGCAGAA TCGGCTTGCT G CTACGAGAG    3840
```

-continued

```
AAGGAAAGAG CGACCACCAC TTGCACTGTG TGAAAAGATA AAAAACAAAT G ATGGCAAGT      3900

TCTCAAGTTA ACTAAATGGA ATCAACCATT ACCAGGCAAA TTCTTGCAAA T ACCAAAATA      3960

CTACTATGCC TTATAAAACA AAATGAAAGC AGGTTAAGAT TTTCTGCTCT G TTTGTATGT      4020

TAATAGAAAT GGAAATACTA AGTATTTTAA TGCTTAGCTA TTGAACAGTA G ACCTAAAAG      4080

GGTTTTAAGC TATTTAAATC TACTTGCTAG TTTTTGCATA TTTTATATAT A TATATATTT      4140

ATATATATAT ATAGTGAGAA GTGAAGAAAA TGTATGGTAC TAAGATTATG C CTTATTGAT      4200

AAATAGATAA ACCAATTTGA ATCCTCTTAG CATGTTTAAG TATGTTGATT G CTTTCTAAT      4260

TAATGAACTT CTCACAGAAA TTTCACTTAG TGAAACCAAT GATTGTAGCA A ACTCATACT      4320

GGATCATTTC AGTTACCTTG AACTAATAGC ACATAATGGT TTTTTGTTGT T GTTGTTTTT      4380

AATGTAGCCC TTACCTGGAT ATACATAGTC TGCAATCACC AAAGTATAAT A TCTTGTAAG      4440

GCTATATTTT TTAAAGCATA TTTTTTCTTG AGCATTAAAT TATCCTAAAT G GTAATATAT      4500

TGTGGATAAG TCTGGGCTTA TTGGACATAA TACATATTTG GGTTGGTACT G GTTGAATCC      4560

TTCAGTTAAC TGCTTTGTTG CTTTTTGCAA GATTTTTTAT CTTAAACATG T CAGGCATCT      4620

TAAGTCACCT TTATACTGTT TTGTTCCTCT GAGTTTCTTT CAGTATGTTA T ACAAATGCC      4680

AGACATAACA TGTAGCAGCC ATACTTGCAT GGAAACTGAC TACACATACA T AATACTGCA      4740

TTTTATTGTA AGGTTTTCAC ATTAATACAG CAATTACCCT GACTAAATTG A GTTTTGTGA      4800

TATATGGAAA ACTTCATTGT AAGAGAATCT TGCATACAAT GTTGACTATT A ACATCCAAA      4860

ATAAAGCATC TGTGTACAAG                                                   4880
```

(2) INFORMATION FOR SEQ ID NO:6:

(i) SEQUENCE CHARACTERISTICS:
        (A) LENGTH: 752 amino acids
        (B) TYPE: amino acid
        (C) STRANDEDNESS: single
        (D) TOPOLOGY: linear (xi) SEQUENCE DESCRIPTION: SEQ ID NO:6:

```
Met Ala Lys Arg Ser Arg Ser Glu Asp Glu A sp Asp Asp Leu Gln Tyr
 1               5                  10                  15

Ala Asp His Asp Tyr Glu Val Pro Gln Gln L ys Gly Leu Lys Lys Leu
            20                  25                  30

Trp Asn Arg Val Lys Trp Thr Arg Asp Glu A sp Asp Lys Leu Lys Lys
        35                  40                  45

Leu Val Glu Gln His Gly Thr Asp Asp Trp T hr Leu Ile Ala Ser His
    50                  55                  60

Leu Gln Asn Arg Ser Asp Phe Gln Cys Gln H is Arg Trp Gln Lys Val
65                  70                  75                  80

Leu Asn Pro Glu Leu Ile Lys Gly Pro Trp T hr Lys Glu Glu Asp Gln
                85                  90                  95

Arg Val Ile Glu Leu Val Gln Lys Tyr Gly P ro Lys Arg Trp Ser Leu
            100                 105                 110

Ile Ala Lys His Leu Lys Gly Arg Ile Gly L ys Gln Cys Arg Glu Arg
        115                 120                 125

Trp His Asn His Leu Asn Pro Glu Val Lys L ys Ser Ser Trp Thr Glu
    130                 135                 140

Glu Glu Asp Arg Ile Ile Tyr Glu Ala His L ys Arg Leu Gly Asn Arg
145                 150                 155                 160

Trp Ala Glu Ile Ala Lys Leu Leu Pro Gly A rg Thr Asp Asn Ser Ile
                165                 170                 175
```

```
Lys Asn His Trp Asn Ser Thr Met Arg Arg Lys Val Glu Gln Glu Gly
            180                 185                 190

Tyr Leu Gln Asp Gly Ile Lys Ser Glu Arg Ser Ser Ser Lys Leu Gln
            195                 200                 205

His Lys Pro Cys Ala Ala Met Asp His Met Gln Thr Gln Asn Gln Phe
            210                 215                 220

Tyr Ile Pro Val Gln Ile Pro Gly Tyr Gln Tyr Val Ser Pro Glu Gly
225                 230                 235                 240

Asn Cys Ile Glu His Val Gln Pro Thr Ser Ala Phe Ile Gln Gln Pro
            245                 250                 255

Phe Ile Asp Glu Asp Pro Asp Lys Glu Lys Lys Ile Lys Glu Leu Glu
            260                 265                 270

Met Leu Leu Met Ser Ala Glu Asn Glu Val Arg Arg Lys Arg Ile Pro
            275                 280                 285

Ser Gln Pro Gly Ser Phe Ser Ser Trp Ser Gly Ser Phe Leu Met Asp
            290                 295                 300

Asp Asn Met Ser Asn Thr Leu Asn Ser Leu Asp Glu His Thr Ser Glu
305                 310                 315                 320

Phe Tyr Ser Met Asp Glu Asn Gln Pro Val Ser Ala Gln Gln Asn Ser
            325                 330                 335

Pro Thr Lys Phe Leu Ala Val Glu Ala Asn Ala Val Leu Ser Ser Leu
            340                 345                 350

Gln Thr Ile Pro Glu Phe Ala Gly Thr Leu Glu Leu Ile Glu Ser Asp
            355                 360                 365

Pro Val Ala Trp Ser Asp Val Thr Ser Phe Asp Ile Ser Asp Ala Ala
            370                 375                 380

Ala Ser Pro Ile Lys Ser Thr Pro Val Lys Leu Met Arg Ile Gln His
385                 390                 395                 400

Asn Glu Gly Ala Met Glu Cys Gln Phe Asn Val Ser Leu Val Leu Glu
            405                 410                 415

Gly Lys Lys Asn Thr Cys Asn Gly Gly Asn Ser Glu Ala Val Pro Leu
            420                 425                 430

Thr Ser Pro Asn Ile Ala Lys Phe Ser Thr Pro Pro Ala Ile Leu Arg
            435                 440                 445

Lys Lys Arg Lys Met Arg Val Gly His Ser Pro Gly Ser Glu Leu Arg
            450                 455                 460

Asp Gly Ser Leu Asn Asp Gly Gly Asn Met Ala Leu Lys His Thr Pro
465                 470                 475                 480

Leu Lys Thr Leu Pro Phe Ser Pro Ser Gln Phe Phe Asn Thr Cys Pro
            485                 490                 495

Gly Asn Glu Gln Leu Asn Ile Glu Asn Pro Ser Phe Thr Ser Thr Pro
            500                 505                 510

Ile Cys Gly Gln Lys Ala Leu Ile Thr Thr Pro Leu His Lys Glu Thr
            515                 520                 525

Thr Pro Lys Asp Gln Lys Glu Asn Val Gly Phe Arg Thr Pro Thr Ile
            530                 535                 540

Arg Arg Ser Ile Leu Gly Thr Thr Pro Arg Thr Pro Thr Pro Phe Lys
545                 550                 555                 560

Asn Ala Leu Ala Ala Gln Glu Lys Lys Tyr Gly Pro Leu Lys Ile Val
            565                 570                 575

Ser Gln Pro Leu Ala Phe Leu Glu Glu Asp Ile Arg Glu Val Leu Lys
            580                 585                 590
```

-continued

```
Glu Glu Thr Gly Thr Asp Leu Phe Leu Lys Glu Glu Asp Glu Pro Ala
        595                 600                 605

Tyr Lys Ser Cys Lys Gln Glu Asn Thr Ala Ser Gly Lys Lys Val Arg
        610                 615                 620

Lys Ser Leu Val Leu Asp Asn Trp Glu Lys Glu Glu Ser Gly Thr Gln
625                 630                 635                 640

Leu Leu Thr Glu Asp Ile Ser Asp Met Gln Ser Glu Asn Arg Phe Thr
                645                 650                 655

Thr Ser Leu Leu Met Ile Pro Leu Leu Glu Ile His Asp Asn Arg Cys
                660                 665                 670

Asn Leu Ile Pro Glu Lys Gln Asp Ile Asn Ser Thr Asn Lys Thr Tyr
        675                 680                 685

Thr Leu Thr Lys Lys Lys Pro Asn Pro Asn Thr Ser Lys Val Val Lys
        690                 695                 700

Leu Glu Lys Asn Leu Gln Ser Asn Cys Glu Trp Glu Thr Val Val Tyr
705                 710                 715                 720

Gly Lys Thr Glu Asp Gln Leu Ile Met Thr Glu Gln Ala Arg Arg Tyr
                725                 730                 735

Leu Ser Thr Tyr Thr Ala Thr Ser Ser Thr Ser Arg Ala Leu Ile Leu
                740                 745                 750
```

(2) INFORMATION FOR SEQ ID NO:7:

(i) SEQUENCE CHARACTERISTICS:
   (A) LENGTH: 16 amino acids
   (B) TYPE: amino acid
   (C) STRANDEDNESS: single
   (D) TOPOLOGY: linear (xi) SEQUENCE DESCRIPTION: SEQ ID NO:7:

```
Arg Gln Ile Lys Ile Phe Phe Gln Asn Arg Arg Met Lys Trp Lys Lys
1               5                   10                  15
```

A-MYB NULL MUTANT TRANSGENIC MICE

This application is a 371 of PCT/US98/06896 filed Apr. 7, 1998, which claims the benefit of U.S. Provisional Application Serial No. 60/043,353 filed Apr. 15, 1997.

FIELD OF THE INVENTION

The invention relates to transgenic non-human animals and transgenic non-human animal cells harboring a transgene containing a mutation in the A-myb gene and having a functionally disrupted A-myb gene locus. The invention further relates to transgenes and targeting constructs used to produce such transgenic animals and cells, methods of using such animals for modeling male infertility disorders, and methods for using such animals to produce transgenic non-human animals and cells including a further transgene.

BACKGROUND OF THE INVENTION

The myb gene family currently consists of three members, named A, B and c-myb. Of these, c-myb is the most extensively studied member. The B-myb and A-myb genes share extensive sequence homology with c-myb.

The myb oncogene was first identified as the transforming gene of Avian Myeloblastosis virus (AMV) which causes myeloblastic leukemia in chickens and transforms myelomonocytic cells in culture (Baluda et al., *Virology* 15: 185–199 (1964); C. Moscovici, *Immunol.* 71: 79–101 (1975)). The normal cellular counterpart of this oncogene, c-myb, is highly conserved and is present in all vertebrate and some invertebrate species examined (Franchini et al., *Proc. Nat. Acad. Sci. USA* 80: 7385–7389 (1983); Katzen et al., *Cell* 41: 449–456 (1985)). Proteins encoded by the viral as well as the cellular myb gene appear to be localized in the nucleus, and these proteins exhibit a sequence-specific DNA-binding activity (Klempnauer et al., *Cell* 37: 537–547 (1984); Boyle et al., *Proc. Nat. Acad. Sci. USA* 81: 42654269 (1984); Moelling et al., *Cell* 40: 983–990 (1985); Biedenkapp et al., *Nature* 335: 835–837 (1988)). Their sequence-specific DNA binding activity and ability to activate transcription of reporter genes linked to certain promoter/enhancer sequences suggest that they act as nuclear transcription factors (Sakura et al., *Proc. Nat. Acad. Sci. USA* 86: 5758–5762 (1989); Dudek et al., *Proc. Nat. Acad. Sci. USA* 89: 1291–1295 (1992)). A-myb in particular has been recognized as a potent transactivator of transcription (Golay et al., *Oncogene* 9: 2469–2479 (1994); Foos et al., *Oncogene* 9: 2481–2488 (1994)). Elimination of c-myb function in vivo, using gene-knock out techniques, has indicated that homozygous c-myb mutant mice fail to show effective fetal hepatic hematopoiesis resulting in the death of mice in utero confirming an essential role for c-myb in fetal hematopoiesis (Mucenski et al., *Cell* 65: 677–689 (1991)).

In contrast to c-myb, whose role in hematopoiesis is well established, little is known about the role of the A-myb gene in development. Human A-myb is expressed in a variety of lymphoid and solid tumors (Shen-Ong et al., *Mol. Cell. Biol.* 6: 380–392 (1986)). Foos et al., *Oncogene* 9: 2481–2488 (1994) have reported ubiquitous expression of A-myb in chicken cell lines. On the other hand, Sleeman, *Oncogene* 8: 1931-194 (1993) reported specific expression of Xenopus A-myb in testis, with very low levels of expression in ovarian tissue.

Murine spermatogenesis is divided into three distinct intervals which include: (1) stem cell proliferation and renewal; (2) meiosis and (3) germ cell differentiation (spermatogenesis). Spermatogenesis in mice occurs in the seminiferous tubule, a specialized epithelium in which spermatogonia are located in close proximity to the basement membrane. Cells at progressively later stages of meiosis and differentiation are situated closer to the tubular lumen. Spermatogenesis in the mouse occurs in twelve distinct histological stages. Each stage consists of a constant pattern of germ cell association. Stage VII of mouse spermatogenesis is a testosterone dependent stage and includes the following cell types: Type A spermatogonia (stem cells) along with preleptotene spermatocytes, usually situated closest to the basement membrane; pachytene spermatocytes (early meiotic cells) located at the intermediate position between basement membrane and the lumen; and step 7 spermatids and step 16 spermatozoa located closest to the lumen.

Recently, it has been demonstrated that A-myb is expressed at high levels in mouse testis where it is transcribed as multiple transcripts, some of which are differentially spliced to code for smaller proteins (Mettus et al., *Oncogene* 9: 3077–3086 (1994)). A high level of expression of A-myb was seen in mouse testis and very low levels of expression were detected in mouse spleen, ovary and brain. As differentiation proceeds and the primary spermatogonia mature into secondary spermatogonia, which in turn maturate into spermatocytes, a distinct downregulation of A-myb expression was seen in in Situ hybridization studies. A-myb was maximally expressed in type A spermatogonia which are located proximal to the basement membrane and preleptotene and pachytene spermatocytes located between the basement membrane and the lumen. Less intense hybridization was also seen with spermatids. Thus, A-myb expression was maximal in proliferating stem cells and early meiotic cells but reduced in spermatids and absent in spermatozoa undergoing terminal differentiation.

Despite these findings, the functional significance of A-myb remains to be established, particularly in spermatogenesis. More complete information concerning the function of A-myb requires studying the effect of the encoded protein, or the lack thereof, in vivo.

Various animals have been produced with germ line foreign DNA, or with altered levels of expression of certain genes. These animals typically have a foreign or mutated gene incorporated into their genome. In one such class of transgenic animal, the so-called homozygous null or "knockout" mutants, expression of an endogenous gene has been suppressed through genetic manipulation.

Transgenic animals generally harbor at least one copy of a transgene either homologously or nonhomologously integrated into an endogenous chromosomal location so as to encode a foreign or mutant protein. Such transgenic animals are usually produced by introducing the transgene or targeting construct into a fertilized egg, or into an embryonic stem (ES) cell which is then injected into an embryo. Introduction of the transgene into the fertilized egg or ES cell is typically performed by microinjection, retroviral infection, electroporation, lipofection, or biolistics. The fertilized egg or embryo is then transferred to an appropriate pseudopregnant female for the duration of gestation. Knockout mutants may be obtained according to this method where the non-native DNA which is introduced comprises a nucleic acid construct that will be used to suppress expression of a particular gene. Such knockout constructs are typically introduced into ES cells.

One problem in the production of transgenic animals is the relatively low rate of success in obtaining incorporation of the transgene into the germline of the host species.

Moreover, while transgenes have been incorporated into fertilized eggs by microinjection, the smaller size of sperm cells makes incorporation of transgenes by injection difficult. What is needed is a method to increase the frequency of first generation transgenic offspring and to provide for the incorporation of transgenes into sperm.

Male infertility continues to be significant reproductive health problem. What is needed is a live animal model which may be used for the study of male infertility, and for screening and evaluation of potential therapeutic agents useful in the treatment of this disorder.

SUMMARY OF THE INVENTION

Accordingly, it is an object of the invention to provide nonhuman animals in which expression of the A-myb gene has been suppressed.

It is an object of the invention to provide nonhuman cells and nonhuman animals containing a homozygous null mutation of the A-myb gene locus.

It is an object of the invention to provide constructs and vectors for producing such cells and animals containing an A-myb homozygous null mutation.

It is a further object of the invention to provide a method for obtaining incorporation of transgenes of interest into sperm cells, and to provide sperm cells so transformed.

It is an object of the invention to provide a method for the production of nonhuman transgenic animals, by utilizing the aforesaid transgenic sperm.

These and other objects of the invention will be apparent to those of ordinary skill in the art from the following disclosure.

In accordance with the foregoing objects, the invention in one aspect is a targeting construct for functionally disrupting an A-myb gene. The targeting construct comprises a polynucleotide containing at least one portion having a sequence that is substantially homologous to a sequence present in or flanking an A-myb gene locus and which, when integrated at the corresponding A-myb gene locus, functionally disrupts expression of A-myb protein from the gene locus. Such targeting constructs, or portions thereof, integrate at the A-myb gene locus by homologous recombination between the endogenous gene locus and the targeting construct.

In one embodiment, the A-myb gene is functionally disrupted by a targeting construct which inserts a sequence, typically into a coding sequence (i.e., exon), wherein the resultant disrupted A-myb gene is substantially incapable of expressing a functional A-myb protein. In one such embodiment, the targeting construct comprises an upstream homology region having a sequence with substantial identity to a first endogenous A-myb gene sequence, a nonhomologous replacement portion, a downstream homology region having a sequence with substantial identity to a second endogenous A-myb gene sequence located downstream from said first endogenous A-myb sequence, wherein the upstream homology region and downstream homology region flank the nonhomologous replacement portion.

The nonhomologous replacement portion of the targeting construct advantageously comprises a positive selection expression cassette, such as neo. The targeting construct further advantageously comprises a negative selection cassette distal to either the upstream homology region or the downstream homology region. The negative selection cassette may comprise, for example, a tk gene.

According to another embodiment, the invention provides a method for generating stem cells having a functionally disrupted endogenous A-myb gene comprising transferring the aforesaid targeting construct into pluripotent stem cells, and selecting for stem cells having a correctly targeted homologous recombination between the targeting construct and an endogenous A-myb gene sequence.

According to yet another embodiment, the invention provides a method for generating nonhuman animals having a functionally disrupted endogenous A-myb gene, comprising the steps of transferring, into a nonhuman blastocyst, stem cells having a correctly targeted homologous recombination between the aforesaid targeting construct and an endogenous A-myb gene sequence; implanting the resultant blastocyst into a pseudopregnant female; and collecting offspring harboring an endogenous A-myb allele having the correctly targeted homologous recombination.

According to another embodiment, the invention provides transgenic nonhuman animals and stem cells having a genome comprising at least one functionally disrupted A-myb gene. The animal or stem cell is preferably homozygous for the functionally disrupted A-myb gene. Such a homozygous transgenic animal or stem cell is substantially incapable of directing the efficient expression of endogenous A-myb. For example, in a preferred embodiment, a transgenic mouse is homozygous for an inactivated endogenous (i.e., naturally occurring) A-myb gene.

According to one embodiment, the transgenic nonhuman animal or stem cell homozygous for a functionally disrupted A-myb gene comprise an A-myb gene disrupted by an integrated targeting construct, e.g., an integrated targeting construct comprising a neo gene.

According to a preferred embodiment of the invention, the transgenic animal is a mouse comprising a genome having a functionally disrupted murine A-myb allele. Preferably, the mouse is homozygous for the functionally disrupted A-myb allele. Such mice do not produce functional A-myb protein and are infertile.

According to another embodiment, a method is provided for generating nonhuman animals producing sperm harboring a desired transgene.

Spermatogonia are obtained from a nonhuman animal which is homozygous for a functionally disrupted endogenous A-myb gene. An A-myb construct comprising a first DNA sequence encoding a functional A-Myb polypeptide and a second DNA sequence encoding the desired transgene of interest, is transferred into the spermatogonia. The spermatogonia harboring the A-myb construct are then introduced into the testes of nonhuman animals which are homozygous for a functionally disrupted endogenous A-myb gene. Fertile individuals are then selected from the animals having received the transfected spermatogonia. Fertile individuals produce sperm harboring the desired transgene.

According to another method for generating nonhuman animals producing sperm harboring a desired transgene, the testis of nonhuman animals which are homozygous for a functionally disrupted endogenous A-myb gene are infected with an expression vector directing the incorporation into the DNA of said infected testes a first DNA sequence encoding a functional A-Myb polypeptide and a second DNA sequence encoding the desired transgene of interest, linked to said first DNA sequence. Fertile individuals are selected from the infected animals. The fertile individuals produce sperm harboring the desired transgene.

The present invention also provides for the treatment of male infertility in those occurrences of the disease which arise from a defect in the A-myb locus. Treatment comprises the transfer of DNA encoding functional A-Myb polypeptide to the cells of the testes, or by administration of functional A-Myb polypeptide directly to the testes.

According to one such treatment method for restoring fertility in a subject who is infertile due to a defect in the A-myb locus, spermatogonia is first obtained from the subject. An A-myb construct is transferred into the obtained spermatogonia. The A-myb construct comprises a DNA sequence encoding a functional A-Myb polypeptide. The spermatogonia harboring the A-myb construct encoding the functional A-Myb polypeptide is introduced into the testes of the individual to obtain production of functional A-Myb polypeptide in the testes.

In another embodiment of an infertility treatment method, fertility in a subject who is infertile due to a defect in the A-myb locus is restored by infecting the testis of the individual with a retrovirus vector. The vector directs the incorporation of a DNA sequence encoding a functional A-Myb polypeptide into the DNA of the infected testes.

In yet another embodiment, fertility is restored in a subject who is infertile due to a defect in the A-myb locus by locally administered a functional A-Myb polypeptide to the testes of the subject, such as by injection into the seminiferous tubules.

The invention is also directed to spermatogonia comprising recombinant DNA encoding a functional A-Myb polypeptide.

As used herein, the term "A-myb gene" or "A-myb gene locus" refers to a region of a chromosome spanning all of the exons which potentially encode the A-myb polypeptide and extending through flanking sequences (e.g., including promoters, enhancers, etc.) that participate in A-myb protein expression. Thus, an A-myb gene locus includes the region spanning from the first exon through the last exon and also includes adjacent flanking sequences (e.g., polyadenylation signals) that may participate in A-myb gene expression.

The terms "functional disruption" or "functionally disrupted" as used herein means that a gene locus comprises at least one mutation or structural alteration such that the functionally disrupted gene is substantially incapable of directing the efficient expression of functional gene product. By way of example but not limitation, an endogenous A-myb gene that has a neo gene cassette integrated into an exon of an A-myb gene is not capable of encoding a functional A-myb protein and is therefore a functionally disrupted A-myb gene locus. Deletion or interruption of essential transcriptional regulatory elements, polyadenylation signals(s), splicing site sequences will also yield a functionally disrupted gene. Functional disruption of an endogenous A-myb gene, may also be produced by other methods (e.g., antisense polynucleotide gene suppression). The term "structurally disrupted" refers to a targeted gene wherein at least one structural (i.e., exon) sequence has been altered by homologous gene targeting (e.g., by insertion, deletion, point mutation(s), and/or rearrangement). Typically, alleles that are structurally disrupted are consequently functionally disrupted. However A-myb alleles may also be functionally disrupted without concomitantly being structurally disrupted, i.e., by targeted alteration of a non-exon sequence such as ablation of a promoter. An allele comprising a targeted alteration that interferes with the efficient expression of a functional gene product from the allele is referred to as a "null allele".

The expression "functional A-Myb polypeptide" means a polypeptide which, upon expression in or administration to A-myb$^{-/-}$ male individuals, is sufficient to restore spermatogenesis and fertility in such individuals.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

The term "complementary to" is used herein to mean that the subject sequence is homologous to all or a portion of a reference polynucleotide sequence. For illustration, the nucleotide sequence "TATAC" corresponds to a reference sequence "TATAC" and is complementary to a reference sequence "GTATA".

The terms "substantially corresponds to", "substantially homologous", or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long.

"Substantially complementary" as used herein refers to a sequence that is complementary to a sequence that substantially corresponds to a reference sequence. In general, targeting efficiency increases with the length of the targeting transgene portion (i.e., homology region) that is substantially complementary to a reference sequence present in the target DNA (i.e., crossover target sequence). In general, targeting efficiency is optimized with the use of isogeneic DNA homology clamps, although it is recognized that the presence of various recombinases may reduce the degree of sequence identity required for efficient recombination.

The term "nonhomologous sequence", as used herein, has both a general and a specific meaning, it refers generally to a sequence that is not substantially identical to a specified reference sequence, and where no particular reference sequence is explicitly identified, it refers specifically to a sequence that is not substantially identical to a sequence of at least about 50 contiguous bases at an endogenous A-myb gene.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

As used herein, the term "targeting construct" refers to a polynucleotide which comprises: (1) at least one homology region having a sequence that is substantially identical to or substantially complementary to a sequence present in a host cell A-myb gene locus, and (2) a targeting region which becomes integrated into an host cell A-myb gene locus by homologous recombination between a targeting construct homology region and said A-myb gene locus sequence. If the targeting construct is a "hit-and-run" or "in-and-out" type construct (Valancius and Smithies (1991) *Mol. Cell.*

Biol. 11: 1402; Donehower et al. (1992) *Nature* 356: 215; (1991) *J. NIH Res.* 3: 59; which are incorporated herein by reference), the targeting region is only transiently incorporated into the endogenous A-myb gene locus and is eliminated from the host genome by selection. A targeting region may comprise a sequence that is substantially homologous to the endogenous A-myb gene sequence and/or may comprise a nonhomologous sequence, such as a selectable marker (i.e., neo, tk, gkt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene".

The terms "homology region" and "homology clamp" as used herein refer to a segment (i.e., a portion) of a targeting construct having a sequence that substantially corresponds to, or is substantially complementary to, a predetermined A-myb gene sequence, which can include sequences flanking said A-myb. A homology region is generally at least about 100 nucleotides long, preferably at least about 250 to 500 nucleotides long, typically at least about 1000 nucleotides long or longer.

The terms "crossover target sequences" or "endogenous target sequences" as used herein refer to A-myb gene sequences that substantially correspond to, or are substantially complementary to, a transgene homology region.

As used herein, the term "targeting region" refers to a portion of a targeting construct which becomes integrated into an endogenous chromosomal location following homologous recombination between a homology clamp and an endogenous A-myb gene sequence. Typically, a targeting region is flanked on each side by a homology clamp, such that a double-crossover recombination between each of the homology clamps and their corresponding endogenous A-myb gene sequences results in replacement of the portion of the endogenous A-myb gene locus by the targeting region; in such double-crossover gene replacement targeting constructs the targeting region can be referred to as a "replacement region". However, some targeting constructs may employ only a single homology clamp (e.g., some "hit-and-run"-type vectors, see, Bradley et al. (1992) *Bio/Technology* 10: 534, incorporated herein by reference).

As used herein, the term "replacement region" refers to a portion of a targeting construct flanked by homology regions. Upon double-crossover homologous recombination between flanking homology regions and their corresponding endogenous A-myb gene crossover target sequences, the replacement region is integrated into the host cell chromosome between the endogenous crossover target sequences. Replacement regions can be homologous (e.g., have a sequence similar to the endogenous A-myb gene sequence but having a point mutation or missense mutation), nonhomologous (e.g., a neo gene expression cassette), or a combination of homologous and nonhomologous regions.

DESCRIPTION OF THE FIGURES

FIG. 9A shows the structure of the pMV-7 vector of Kirschmeier et al., *DNA* 7, 219–225 (1988).

FIG. 9B shows the structure of the modified pMV-7 vector pMV-7 Δ ClaI/neo E/H, generated by excision of the neo cassette from pMV-7 of FIG. 9A by ClaI digest and placement of the cassette at the Eco RI/Hind III cloning site of pMV-7.

FIG. 9C shows the structure of the vector pMV-7 Δ ClaI/neo E/H-A-myb, formed by insertion of the 6.7 kbp fragment SEQ ID NO:4 into the ClaI site of the FIG. 9B vector. The insert contains the A-myb promoter (cross-hatch), the A-myb coding sequence, and a polyadenylation signal from the bovine growth hormone gene (solid). Arrows in FIGS. 9A–9C indicate transcription start sites.

DETAILED DESCRIPTION OF THE INVENTION

Figure 1:
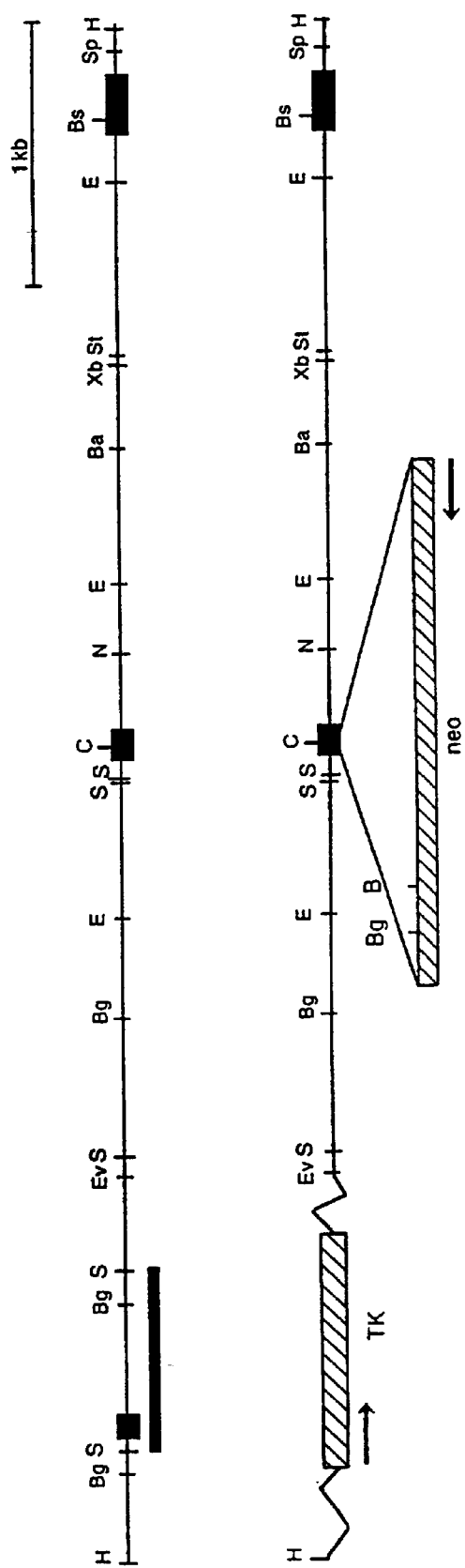
FIG. 1 is a restriction map of an A-myb genomic clone (top), and the structure of a targeting vector (bottom). The coding exons are depicted by black boxes. The black boxes in the restriction map represent A-myb exons 3, 4 and 5. A genomic fragment comprising the entire exon 3 and a portion of intron 3 was obtained by digestion of the clone with SspI. The clone, which was used as a probe, is shown as a black bar. The arrows depict the transcriptional orientation of the neo (neomycin transferase gene) and tk (thymidine kinase) genes. Bg, BglII; S, SspI; Ev, EcoRV; E, EcoRI; C, ClaI; N, NcoI; Ba, BanI; Xb, XbaI; St, StuI; Bs, BstXII; H, HindIII; B, BamHI.

Chimeric targeted mice may be derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells may be manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989), each of which is incorporated herein by reference).

Oligonucleotides can be synthesized on an Applied Bio-Systems oligonucleotide synthesizer according to specifications provided by the manufacturer.

According to the practice of the invention, the endogenous A-myb alleles of a cell line or nonhuman animal are functionally disrupted so that expression of endogenously encoded A-myb gene is suppressed or eliminated. In general, polynucleotide constructs are employed for this purpose. Methods for accomplishing this result are described in detail in WO 95/11968 with respect to transgenic non-human animals and mammalian cells hosting a transgene encoding an amyloid precursor protein (APP) and "knock out" mutants thereof. The entire disclosure of WO 95/11968 is incorporated herein by reference. Similar methods of preparing transgenic non-human animals and mammalian cells characterized by knock-out mutations are described in WO 94/06908 (targeting of lymphocyte transduction gene expression) and, WO 94/28123 (targeting of CD28 expression), the entire disclosures of which are incorporated herein by reference.

Gene targeting, which is a method of using homologous recombination to modify a mammalian genome, can be used to introduce genetic changes into cultured cells. By targeting a gene of interest in embryonic stem (ES) cells, these changes can be introduced into the germlines of laboratory animals to study the effects of the modifications on whole organisms, among other uses. The gene targeting procedure is accomplished by introducing into tissue culture cells a DNA targeting construct that has a segment homologous to a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its chromosomal counterpart in the ES cell genome. The targeting constructs are typically arranged so that they insert an additional sequence, such as a positive selection marker, into coding elements of the target gene, thereby functionally disrupting it. Targeting constructs usually are insertion-type or replacement-type constructs (Hasty et al. (1991) *Mol. Cell. Biol.* 11: 4509).

The invention encompasses production of stem cells and nonhuman animals that have the endogenous A-myb gene inactivated by gene targeting with a homologous recombination targeting construct. The A-myb gene sequence may be used as a basis for producing PCR primers that flank a region that will be used as a homology clamp in a targeting construct. The PCR primers are then used to amplify a genomic sequence from a genomic clone library or from a preparation of genomic DNA, preferably from the strain of nonhuman animal that is to be targeted with the targeting construct. The amplified DNA is then used as a homology clamp and/or targeting region. General principles regarding the construction of targeting constructs and selection methods are reviewed in Bradley et al. (1992) *Bio/Technology* 10: 534, incorporated herein by reference.

The isolation of A-myb genomic DNA useful for this purpose is described herein. Appropriate probes may be designed based on known A-myb cDNA nucleotide sequences. For example, the complete nucleotide sequence of the mouse A-myb cDNA (SEQ ID NO:1), deduced amino acid sequence (SEQ ID NO:2), and cDNA restriction map are disclosed in Mettus et al., *Oncogene* 9: 3077–3086 (1994), the entire disclosure of which is incorporated herein by reference. The encoded mouse A-myb protein contains 751 amino acids (SEQ ID NO:2) and has an estimated molecular weight of 83 kDa. It may be appreciated that A-myb genomic DNA may be derived using an appropriate cDNA fragment as a probe to identify and isolate genomic A-myb from an appropriate genomic DNA library.

Targeting constructs can be transferred into pluripotent stem cells, such as ES cells, wherein the targeting constructs homologously recombine with a portion of the endogenous A-myb gene locus and create mutation(s) (i.e., insertions, deletions, rearrangements, sequence replacements, and/or point mutations) which prevent the functional expression of the endogenous A-myb gene.

One method is to delete, by targeted homologous recombination, essential structural elements of the endogenous A-myb gene. For example, a targeting construct can homologously recombine with an endogenous A-myb gene and delete a portion spanning substantially all of one or more exons to create an exon-depleted allele, typically by inserting a replacement region lacking the corresponding exon(s). Transgenic animals homozygous for the exon-depleted allele (e.g., by breeding of heterozygotes to each other) are essentially incapable of expressing a functional endogenous A-myb polypeptide. Similarly, homologous gene targeting can be used, if desired, to functionally disrupt the A-myb gene by deleting only a portion of an exon.

Targeting constructs can also be used to delete essential regulatory elements of the endogenous A-myb gene, such as promoters, enhancers, splice sites, polyadenylation sites, and other regulatory sequences, including cis-acting sequences that may occur upstream or downstream of the A-myb structural gene but which participate in endogenous A-myb gene expression. Deletion of regulatory elements is typically accomplished by inserting, by homologous double-crossover recombination, a replacement region lacking the corresponding regulatory element(s).

The mouse A-myb gene was isolated by screening a λ DASH mouse genomic library derived from the 129/J mouse strain, using a probe derived from the 5' end of the A-myb cDNA clone (Mettus et al., *Oncogene* 9, 3077–3086, 1994) that encodes the DNA binding domain of the protein. Positive clones that contained a 5.9 kbp HindIII fragment were subcloned into pGEM 7Zf(+) plasmid vector. The complete nucleotide sequence of this 5.9 kbp clone was determined using the method of Sanger et al., *Proc. Natl.*

*Acad. Sci. USA* 74, 5463–5467 (1977). The sequence analysis showed that this fragment contained exons 3,4 and 5 of the gene that code for the 5' end of the DNA binding domain of the protein (FIG. 1, top). The complete nucleotide sequence of this 5.9 kbp clone is SEQ ID NO:3.

While the A-myb promoter does not contain a putative TATA or CCAT box, it contains a highly GC rich sequence, a feature observed with many testis-specific and housekeeping gene promoters.

A preferred method is to interrupt essential structural and/or regulatory elements of the endogenous A-myb gene by targeted insertion of a polynucleotide sequence, and thereby functionally disrupt the endogenous A-myb gene. For example, a targeting construct can homologously recombine with the endogenous A-myb gene and insert a nonhomologous sequence, such as a neo expression cassettes into a structural element (e.g., an exon) and/or regulatory element (e.g., enhancer, promoter, splice site, polyadenylation site) to yield a targeted A-myb allele having an insertional interruption. The inserted sequence can range in size from about 1 nucleotide (e.g., to produce a frameshift in an exon sequence) to several kilobases or more, as limited by efficiency of homologous gene targeting with targeting constructs having a long nonhomologous replacement region.

One preferred target site is the DNA binding domain of the A-myb gene. The DNA binding domain in the A-myb protein spans amino acids tryptophan-32 to valine-188, corresponding to nucleotides 352 to 820 of the murine A-myb cDNA. See SEQ ID NO:1.

Targeting constructs can also be employed to replace a portion of the endogenous A-myb gene with an exogenous sequence (i.e., a portion of a targeting transgene); for example, a first exon of an A-myb gene may be replaced with a substantially identical portion that contains a nonsense or missense mutation.

A targeting construct may be transferred by electroporation of microinjection into a totipotent ES cell line. The targeting construct homologously recombines with endogenous sequences in or flanking of the A-myb gene locus and functionally disrupts at least one allele of the A-myb gene. Typically, homologous recombination of the targeting construct with endogenous A-myb locus sequences will result in integration of a nonhomologous sequence encoding and expressing a selectable marker, such as neo, usually in the form of a positive selection cassette. ES cells having at least one such A-myb null allele are selected for by propagating the cells in a medium that permits the preferential propagation of cells expressing the selectable marker. Selected ES cells are examined by PCR analysis and/or Southern blot analysis to verify the presence of a correctly targeted A-myb allele. Breeding of nonhuman animals which are heterozygous for a null allele may be performed to produce nonhuman animals homozygous for said null allele, so-called "knockout" animals (Donehower et al. (1992) *Nature* 256: 215; *Science* 256: 1392, incorporated herein by reference). Alternatively ES cells homozygous for a null allele having an integrated selectable marker can be produced in culture by selection in a medium containing high levels of the selection agent (e.g., G418 or hygromycin). Heterozygosity and/or homozygosity for a correctly targeted null allele can be verified with PCR analysis and/or Southern blot analysis of DNA isolated from an aliquot of a selected ES cell clone and/or from tail biopsies.

Gene targeting techniques which have been described, include but are not limited to: co-electroporation, "hit-and-run", single-crossover integration, and double-crossover recombination (Bradley et al. (1992) *Bio/Technology* 10: 534). The preparation of the homozygous A-myb null mutants can be practiced using essentially any applicable homologous gene targeting strategy known in the art. The configuration of a targeting construct depends upon the specific targeting technique chosen. For example, a targeting construct for single-crossover integration or "hit-and-run" targeting need only have a single homology clamp linked to the targeting region, whereas a double-crossover replacement-type targeting construct requires two homology clamps, one flanking each side of the replacement region.

For example and not limitation, a targeting construct comprises, in order: (1) a first homology clamp having a sequence substantially identical to a sequence within about 3 kilobases upstream (i.e., in the direction opposite to the transnational reading frame of the exons) of an exon of an endogenous A-myb gene, (2) a replacement region comprising a positive selection cassette having a pgk promoter driving transcription of a neo gene, (3) a second homology clamp having a sequence substantially identical to a sequence within about 3 kilobases downstream of said exon of said endogenous A-myb gene, and (4) a negative selection cassette, comprising a PGK promoter driving transcription of an HSV tk gene. Such a targeting construct is suitable for double-crossover replacement recombination which deletes a portion of the endogenous A-myb locus spanning said exon and replaces it with the replacement region having the positive selection cassette. The deleted exon is one which is essential for expression of a functional A-myb gene product. Thus, the resultant exon-depleted allele is functionally disrupted and is termed a null allele.

Targeting constructs comprise at least one homology clamp linked in polynucleotide linkage (i.e., by phosphodiester bonds) to a targeting region. A homology clamp has a sequence which substantially corresponds to, or is substantially complementary to, an endogenous A-myb gene sequence of a nonhuman host animal, and may comprise sequences flanking the A-myb gene.

Although no lower or upper size boundaries for recombinogenic homology clamps for gene targeting have been conclusively determined in the art, the best mode for homology clamps is believed to be in the range between about 50 bp and several tens of kilobases. Consequently, targeting constructs are generally at least about 50 to 100 nucleotides long, preferably at least about 250 to 500 nucleotides long, more preferably at least abut 1000 to 2000 nucleotides long, or longer. Construct homology regions (homology clamps) are generally at least about 50 to 100 bases long, preferably at least about 100 to 500 bases long, and more preferably at least about 750 to 2000 bases long. It is believed that homology regions of about 7 to 8 kilobases in length are preferred with one preferred embodiment having a first homology region of about 7 kilobases flanking one side of a replacement region and a second homology region of abut 1 kilobase flanking the other side of said replacement region. The length of homology (i.e., substantial identity) for a homology region may be selected at the discretion of the practitioner on the basis of the sequence composition and complexity of the endogenous A-myb gene target sequence (s) and guidance provided in the art. Targeting constructs have at least one homology region having a sequence that substantially corresponds to, or is substantially complementary to, an endogenous A-myb gene sequence (e.g., an exon sequence, an enhancer, a promoter, an intronic sequence, or a flanking sequence within about 3–20 kb of the A-myb gene). Such a targeting construct homology region serves as a template for homologous pairing and recombination with substantially identical endogenous A-myb gene sequence(s). In targeting constructs, such homology regions typically flank the replacement region, which is a region of the targeting construct that is to undergo replacement with the targeted endogenous A-myb gene sequence. Thus, a segment of the targeting construct flanked by homology regions can replace a segment of an endogenous A-myb gene sequence by double-crossover homologous recombination. Homology regions and targeting regions are linked together in conventional linear polynucleotide linkage (5' to 3' phosphodiester backbone). Targeting constructs are generally double-stranded DNA molecules, most usually linear.

Homology regions are generally used in the same orientation (i.e., the upstream direction is the same for each homology region of a transgene to avoid rearrangements). Double-crossover replacement recombination thus can be used to delete a portion of the endogenous A-myb and concomitantly transfer a nonhomologous portion (i.e., a neo gene expression cassette) into the corresponding chromosomal location. Double-crossover recombination can also be used to add a nonhomologous portion into the endogenous A-myb gene without deleting endogenous chromosomal portions. However, double-crossover recombination can also be employed simply to delete a portion of an endogenous gene sequence without transferring a nonhomologous portion into the endogenous A-myb gene. Upstream and/or downstream from the nonhomologous portion may be a gene which provides for identification of whether a double-crossover homologous recombination has occurred; such a gene is typically the HSV tk gene which may be used for negative selection.

Typically, targeting constructs used for functionally disrupting endogenous A-myb genes will comprise at least two homology regions separated by a nonhomologous sequence which contains an expression cassette encoding a selectable marker, such as neo (Smith and Berg (1984) *Cold Spring Harbor Symp. Quant. Biol.* 49: 171; Sedivy and Sharp (1989) *Proc. Natl. Acad. Sci.* (*U.S.A.*) 86: 227; Thomas and Capechi (1987), *Cell* 51: 503). However, some targeting transgenes may have the homology region(s) flanking only one side of a nonhomologous sequence. Targeting transgenes of the invention may also be of the type referred to in the art as "hit-and-run" or "in-and-out" transgenes (Valancius and Smithies (1991) *Mol. Cell. Biol.* 11: 1402; Donehower et al. (1992) *Nature* 356: 215; (1991) *J.NIH Res.* 3: 59; which are incorporated herein by reference).

The positive selection expression cassette encodes a selectable marker which affords a means for selecting cells which have integrated targeting transgene sequences spanning the positive selection expression cassette. The negative selection expression cassette encodes a selectable marker which affords a means for selecting cells which do not have an integrated copy of the negative selection expression cassette. Thus, by a combination positive-negative selection protocol, it is possible to select cells that have undergone homologous replacement recombination and incorporated the portion of the transgene between the homology regions (i.e., the replacement region) into a chromosomal location by selecting for the presence of the positive marker and for the absence of the negative marker (Valancius and Smithies, supra).

An expression cassette typically comprises a promoter which is operational in the targeted host cell (e.g., ES cell) linked to a structural sequence that encodes a protein or polypeptide that confers a selectable phenotype on the targeted host cell, and a polyadenylation signal. A promoter included in an expression cassette may be constitutive, cell type-specific, stage-specific, and/or modulatable (e., by hormones such as glucocorticoids; MMTV promoter), but is expressed prior to and/or during selection. An expression cassette can optionally include one or more enhancers, typically linked upstream of the promoter and within about 3–10 kilobases. However, when homologous recombination at the targeted endogenous site(s) places the nonhomologous sequence downstream of a functional endogenous promoter, it may be possible for the targeting construct replacement region to comprise only a structural sequence encoding the selectable marker, and rely upon the endogenous promoter to drive transcription (Doetschman et al. (1988) *Proc. Natl. Acad. Sci.* (*U.S.A.*) 85: 8583; incorporated herein by reference). Similarly, an endogenous enhancer located near the targeted endogenous site may be relied on to enhance transcription of transgene sequences in enhancerless transgene constructs.

Preferred expression cassettes for inclusion in the targeting constructs encode and express a selectable drug resistance marker and/or a HSV thymidine kinase (tk) enzyme. Suitable drug resistance genes include, for example: gpt (xanthine-guanine phosphoribosytltransferase), which can be selected for with mycophenolic acid; neo (neomycin phosphotransferase), which can be selected for with G418 or hygromycin; and DFHR (dihydrofolate reductase), which can be selected for with methotrexate (Mulligan and Berg (1981) *Proc. Natl. Acad. Sci.* (*U.S.A.*) 78: 2072; Southern and Berg (1982) *J. Mol. Appl. Genet.* 1: 327; which are incorporated herein by reference).

Selection for correctly targeted recombinants will generally employ at least positive selection, wherein a nonhomologous expression cassette encodes and expresses a functional protein (e.g., neo or gpt) that confers a selectable phenotype to targeted cells harboring the endogenously integrated expression cassette, so that, by addition of a selection agent (e.g., G418 or mycophenolic acid) such targeted cells have a growth or survival advantage over cells which do not have an integrated expression cassette.

It is preferable that selection for correctly targeted homologous recombinants also employ negative selection, so that cells bearing only nonhomologous integration of the transgene are selected against. Typically, such negative selection employs an expression cassette encoding the herpes simplex virus thymidine kinase gene (HSV tk) positioned in the transgene so that it should integrate only by nonhomologous recombination. Such positioning generally is accomplished by linking the HSV tk expression cassette (or other negative selection cassette) distal to the recombinogenic homology regions so that double-crossover replacement recombination of the homology regions transfers the positive selection expression cassette to a chromosomal location but does not transfer the HSV tk gene (or other negative selection cassette) to a chromosomal location. A nucleoside analog, ganciclovir, which is preferentially toxic to cells expressing HSV tk, can be used as the negative selection agent, as it selects for cells which do not have an integrated HSV tk expression cassette. FIAU may also be used as a selective agent to select for cells lacking HSV tk.

In order to reduce the background of cells having incorrectly integrated targeting construct sequences, a combination positive-negative selection scheme is typically used (Mansour et al., *Nature* 336: 348–352 (1988) incorporated herein by reference). Positive-negative selection involves the use of two active selection cassettes: (1) a positive one (e.g., the neo gene), that can be stably expressed following either random integration or homologous targeting, and (2)

a negative one (e.g., the HSV tk gene), that can only be stably expressed following random integration, and cannot be expressed after correctly targeted double-crossover homologous recombination. By combining both positive and negative selection steps, host cells having the correctly targeted homologous recombination between the transgene and the endogenous A-myb gene can be obtained.

Generally targeting constructs preferably include: (1) a positive selection expression cassette flanked by two homology regions that are substantially identical to host cell endogenous A-myb gene sequences, and (2) a distal negative selection expression cassette. However, targeting constructs which include only a positive selection expression cassette can also be used. Typically, a targeting construct will contain a positive selection expression cassette which includes a neo gene linked downstream (i.e., towards the carboxy-terminus of the encoded polypeptide in transnational reading frame orientation) of a promoter such as the HSV tk promoter or the pgk promoter. More typically, the targeting transgene will also contain a negative selection expression cassette which includes an HSV tk gene linked downstream of a PGK promoter.

FIG. 1 (bottom) is a schematic representation of a typical positive-negative A-myb targeting construct. FIG. 1 (bottom) shows the placement of neo and tk ("TK") genes. Arrows mark the transcriptional orientation of the neo and tk genes. FIG. 1 (top) is a schematic representation of the Hind III 5.9 kbp genomic clone used to generate the targeting construct of FIG. 1 (bottom). Black boxes in the restriction maps of FIG. 1 represent exons.

The targeting construct of FIG. 1 (bottom) was deposited in the Unites States Department of Agriculture Northern Research Laboratories, Peoria, Ill. under accession number B21576 on May 1, 1996. The HindIII 5.9 kbp genomic clone used to generate the targeting construct was deposited in the same depository, on the same date, under accession number B21575. The nucleotide sequence of the 5.9 kbp clone is SEQ ID NO:3.

Typically, targeting polynucleotides of the invention have at least one homology region that is at least about 50 nucleotides long, and it is preferable that homology regions are at least about 75 to 100 nucleotides long, and more preferably at least about 200–2000 nucleotides long, although the degree of sequence homology between the homology region and the targeted sequence and the base composition of the targeted sequence will determine the optimal and minimal homology region lengths (e., G-C rich sequences are typically more thermodynamically stable and will generally require shorter homology region length). Therefore, both homology region length and the degree of sequence homology can only be determined with reference to a particular predetermined sequence, but homology regions generally must be at least about 50 nucleotides long and must also substantially correspond or be substantially complementary to a predetermined endogenous target sequence. Preferably, a homology region is at least about 100 nucleotides long and is identical to or complementary to a predetermined target sequence in or flanking the A-myb gene. If it is desired that correctly targeted homologous recombinants are generated at high efficiency, it is preferable that at least one homology region is isogeneic (i.e., has exact sequence identity with the crossover target sequence(s) of the endogenous A-myb gene), and is more preferred that isogeneic homology regions flank the exogenous targeting construct sequence that is to replace the targeted endogenous A-myb sequence.

The A-myb sequence may be scanned for possible disruption sites. Plasmids are engineered to contain an appropriately sized construct replacement sequence with a deletion or insertion in the A-myb gene and at least one flanking homology region which substantially corresponds or is substantially complementary to an endogenous target DNA sequence. Typically, two flanking homology regions are used, one on each side of the replacement region sequence. For example, one homology region may be substantially identical to a sequence upstream (i.e., the direction towards the transcription start site(s) of the murine A-myb exon 4 and a second homology region may be substantially identical to a sequence downstream of the murine A-myb exon 4.

The A-myb gene is inactivated by homologous recombination in a pluripotent cell line that is capable of differentiating into germ cell tissue. A DNA construct, as discussed above, that contains an altered copy of a mouse A-myb gene is introduced into the nuclei of ES cells. In a portion of the cells, the introduced DNA recombines with the endogenous copy of the mouse A-myb gene, replacing it with the altered copy. Cells containing the newly engineered genetic lesion are injected into a host mouse embryo, which is reimplanted into a recipient female. Some of these embryos develop into chimeric mice that possess germ cells derived from the mutant cell line. Therefore, by breeding the chimeric mice it is possible to obtain a new line of mice containing the introduced genetic lesion.

Vectors containing a targeting construct are typically grown in *E. coli* and then isolated using standard molecular biology methods, or may be synthesized as oligonucleotides. Direct targeted inactivation which does not require prokaryotic or eukaryotic vectors may also be performed. Targeting constructs can be transferred to host cells by any suitable technique, including microinjection, electroporation, lipofection, biolistics, calcium phosphate precipitation, and viral-based vectors, among others. Other methods used to transform mammalian cells include the use of Polybrene, protoplast fusion, and others (e.g., generally, Sambrook et al. Molecular Cloning: A Laboratory Manual, 2d ed., 1989, Cold Spring Harbor Laboratory Press, Cold Spring Harbor, N.Y., which is incorporated herein by reference).

For making transgenic non-human animals (which include homologously targeted non-human animals), embryonal stem cells (ES cells) are preferred. Murine ES cells, such as AB-1 line grown on mitotically inactive SNL76/7 cell feeder layers (McMahon and Bradley (1990) *Cell* 62: 1073) essentially as described (Robertson, E. J. (1987) in *Teratocarcinomas and Embryonic Stem Cells: A Practical Approach*. E. J. Robertson, ed. (Oxford: IRL Press), p. 71–112) may be used for homologous gene targeting. Other suitable ES lines include but are not limited to, the E14 line (Hooper et al. (1987) *Nature* 326: 292–295), the D3 line (Doetschman et al. (1985) *J. Embryol. Exp. Morphi.* 87: 27–45), and the CCE line (Robertson et al. (1986) *Nature* 323: 445–448). The practice of the present invention is specifically exemplified hereinafter using ES cells of mouse strain 129/J (Jackson Laboratories). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having an inactivated endogenous A-myb locus and are backcrossed and screened for the presence of the correctly targeted transgene(s) by PCR or Southern blot analysis on tail biopsy DNA of offspring so as to identify transgenic mice-heterozygous for the inactivated A-myb. By performing the appropriate crosses, it is possible to produce a transgenic nonhuman animal homozygous for functionally disrupted A-myb alleles. Such transgenic animals are substantially incapable of making an endogenous A-myb gene product.

The functionally disrupted A-myb homozygous null mutant transgenic animals will typically comprise rats or mice, but nonmurine species such as dogs, cattle, sheep, goats, pigs and nonhuman primates, for example, may be utilized.

Homozygous null male A-myb animals are infertile due to a block in spermatogenesis. Histopathological examination of testes from A-myb$^{-/-}$ mice of the present invention indicates that the differentiation of spermatogonia is arrested at the pachytene stage of meiosis, indicating an essential role for A-myb in male germ cell differentiation. It appears that A-myb is essential for transition of spermatogonia to the spermatid stage. The results described herein show that the proliferation of primary germ cells is not dependent on the presence of A-myb but that their differentiation is dependent on the synthesis of the A-Myb protein. Loss of A-Myb does not seem to affect the formation of Leydig and Sertoli cells. Earlier studies (Mettus et al., *Oncogene* 9, 3077–3086, 1994) have shown that A-myb is not expressed in Sertoli cells or Leydig cells. These cells appear normal in A-myb$^{-/-}$ mice.

The histopathology of the testis seen in A-myb$^{-/-}$ mice is surprisingly similar to the histopathology seen in a large percentage of men who are infertile (Rosai, J., "Testis" in *Ackerman's Surgical Pathology*, G. Stamathis ed. (C. V. Mosby Co.), pp. 949–982, 1989; Soderstrom and Suominen, *Arch. Pathol. Lab. Med.* 104, 476–482, 1980; Wong, et al., *Arch. Pathol.* 95, 151–159, 1973). Biopsy specimens from infertile men with total lack of spermatozoa usually show one of the following conditions: (1) germ cell aplasia (Sertoli cell-only syndrome), in which the tubules are populated by Sertoli cells only and there is a complete absence of germ cells; (2) spermatocystic arrest, characterized by a halt of the maturation sequence, usually at the stage of the primary and secondary spermatocyte development where no spermatids or spermatozoa are present; and (3) generalized fibrosis which appears to result in obstructive azoospermia due to bilateral obstruction or absence of some part of the duct system. The testicular histopathology of A-myb$^{-/-}$ mice is indistinguishable from the histopathology of biopsies described in infertile men suffering from spermatocystic arrest, suggesting that defects in A-myb expression or function may constitute the molecular basis of this form of human infertility.

The ovaries of the A-myb$^{-/-}$ female mice appear normal by histological assessment which is further evidence by the ability of these mice to become pregnant and deliver pups. However, a striking abnormality was observed in the female A-myb$^{-/-}$ mice following the birth of the pups. Examination of the mothers revealed complete absence of milk formation following the delivery of pups. Pathological examination of the A-myb$^{-/-}$ mothers 48 hours following delivery revealed severe impairment of mammary epithelial proliferation in mutant mice following pregnancy.

Development of mouse mammary epithelium occurs in two stages. The first stage of development occurs during puberty, when the breast tissue becomes fully developed and is characterized by ductal elongation. The ductal cells at this stage express estrogen receptors and the ductal elongation is believed to be stimulated by estrogens. Following sexual maturation, the mammary epithelial cells acquire progesterone receptors and at this stage of development, require both estrogen and progesterone for proliferation. During pregnancy, the combined action of estrogens and progesterone results in ductal side branching and lobuloalveolar development. The mammary glands of A-myb$^{-/-}$ mice appeared to develop normally during sexual maturation, as evidenced by histological analysis. However, during pregnancy, the proliferation of mammary epithelium was considerably diminished in the A-myb$^{-/-}$ mice. This appeared to be due to reduced cell proliferation resulting in diminished ductile branching following pregnancy. These results indicate that A-myb may play a critical role in steroid-induced proliferation of mammary epithelium during pregnancy.

The A-myb$^{-/-}$ male animals of the invention may be utilized as a model for male infertility, and for studying spermatogenesis. The A-myb$^{-/-}$ animals may be used in the screening of potential therapeutic synthetic A-myb peptides. Such peptides could be screened for the ability to induce resumption of spermatogenesis upon local administration to the testes of A-myb$^{-/-}$ mice. The candidate peptide would be administered locally by injection into the testes of the A-myb$^{-/-}$ mice.

The A-myb$^{-/-}$ animals of the invention may also be used as host animals for the transfer of desired transgenes via the sperm of A-myb$^{-/-}$ individuals rescued with a transgene construct encoding non-defective A-myb gene and the desired additional transgene. The A-myb$^{-/-}$ animals described herein contain immature germ cells. Since these are stem cells, they have the potential for self renewal and thus undergo replication. These cells may be induced to replicate and undergo differentiation to mature spermatids upon the introduction of exogenous A-myb.

Accordingly, spermatogonia are isolated from the A-myb$^{-/-}$ animals, cultured in vitro and then transfected with a transgene construct comprising a first DNA sequence encoding a functional A-Myb polypeptide which is linked to a second DNA sequence comprising the transgene of interest, the expression of which is desired in the animal's germline. The first and second DNA sequences may be operatively linked in that the transcription of both sequences is under the control of the same promoter or enhancer. Alternatively separate promoter/enhancer elements may be included in the construct for the first and second DNA sequences.

The transfected cells are then reintroduced into the testes of the A-myb$^{-/-}$ animals. This will allow for expression of A-myb and the continuation of spermatogenesis, resulting in the production of viable spermatozoa which include the transgene of interest. While not necessarily required, it is preferred that the spermatogonia donor and transfected cell recipient are of the same species, preferably the same strain.

The practice of the present invention is exemplified herein using the neo gene as the transgene. It may be appreciated that it is possible to generate nonhuman animals producing sperm which harbor any desired transgene, provided the transgene may be contained in a construct further including a wild type A-myb gene. Spermatogonia which fail to incorporate the transgene construct encoding the wild type A-myb gene and the transgene of interest will not mature into spermatozoa. Spermatogonia which successfully incorporate the construct are "rescued" by the A-myb wild type transgene, but will also contain the additional transgene of interest. Since only immature germs cells which are "rescued" by the transgene construct are able to mature into spermatozoa competent for fertilization, the sperm output of the rescued animal is limited to cells which have successfully incorporated the construct and the transgene of interest. The A-myb$^{-/-}$ animals "rescued" with the transgene construct thus possess transgenic sperm, which can pass the desired transgene to offspring. Alternatively, the transgenic spermatozoa can be harvested and used to artificially inseminate females, or to fertilize eggs in vitro.

Accordingly, spermatogonia are isolated from A-myb$^{-/-}$ animals, cultured in vitro, and transfected with an appropriate "rescue" construct containing wild-type A-myb DNA and the transgene of interest. The transfected cells are then reintroduced into the testis of A-myb$^{-/-}$ animals.

Spermatogonia may be isolated from A-myb$^{-/-}$ animals according to known methods. Methods for isolating germ cells from the testis of mammals are known to the art. See, e.g., Ogawa et al., *J. Dev. Biol.* 41, 111–122 (1997); Brinster and Zimmermann, *Proc. Natl. Acad. Sci. USA* 91, 11298–302 (1994); Brinster and Avarbock, *Proc. Natl. Acad. Sci. USA* 91, 11303–7 (1994); Hofmann et al., *Exp. Cell Res.* 201:417–435 (1992); Hofmann et al., *Proc. Natl. Acad. Sci. USA* 91, 5333–7 (1994). The entire disclosures of the preceding references are incorporated herein by reference.

The isolated spermatogonia are transfected with a rescue construct containing A-myb DNA encoding a functional A-Myb polypeptide, e.g. cDNA, under the control of a promoter to obtain A-myb expression, and a transgene of interest. The construct includes structural sequences encoding the functional A-Myb polypeptide and the transgene of interest, and linked regulatory elements that drive expression of both structural sequences in the host. At least one promoter/enhancer is linked upstream of the first structural sequence in an orientation to drive transcription of the A-myb wild-type DNA and transgene of interest. The promoter is selected so as to provide for expression of the transgenes in the testis. While the PGK2 and CMV promoter/enhancer elements are known to be capable of driving constitutive gene expression in the testis (Robinson et al., *Proc. Natl. Acad. Sci. USA* 86, 8437–41, 1989; Rosenberg et al., *Cell Growth & Differ.* 1995; Goto et al., *Exp. Cell Res.* 186, 273–8, 1990), it is preferred that the promoter drive expression at levels similar to the naturally occurring A-myb gene, and the promoter is selected accordingly. Most advantageously, the promoter comprises the naturally occurring A-myb promoter.

The rescue construct generally encodes the full-length A-Myb protein, or fragment or analog thereof, having sufficient A-Myb activity to permit spermatogenesis to proceed in the host. Preferably, the A-Myb-encoding DNA encodes the full-length protein. The transgene of interest may be designed so as to provide for the expression of any desired gene in the rescued host animal.

To express A-myb selectively rather than constitutionally, a 10 kbp HindIII genomic fragment containing the A-myb promoter region is isolated from a lambda phage mouse genomic library using $^{32}$P-labeled A-myb cDNA as a probe. The HindIII genomic fragment is further cleaved with BstEII to generate a HindIII/BstEII fragment containing the A-myb promoter/enhancer region. The HindIII/BstEII fragment may be cloned into the BstEII site of an A-myb cDNA clone.

The isolated A-myb$^{-/-}$ spermatogonia may be transfected with the rescue construct by methods known to those skilled in the art such as by the calcium phosphate method (Chen and Okayama, *Mol. Cell. Biol.* 7, 2745–52, 1987), the electroporation method (Potter, *Anal. Biochem* 74, 361–373, 1988; Zheng and Chang, *Biochim. Biophys. Acta* 1088, 104–110, 1991) the liposome-mediated method (Lopata et al., *Nucl. Acids Res.* 12, 5705, 1984) or the DEAE-dextran method (Felgner et al., *Proc. Natl. Acad. Sci. USA* 84, 7413–7, 1987). The entire disclosures of the aforementioned references are incorporated herein by reference.

After overnight incubation at 37° C., the transfected cells are then introduced into the seminiferous tubules in the testes of A-myb$^{-/-}$ mice, such as according to the procedure of Brinster and Zimmermann Brinster, supra. As an alternative to injection into the seminiferous tubules, the transfected cells may be injected into the rete testis (Ogawa et al., *Int. J. Dev. Biol.* 41, 111–122 (1997), the entire disclosure of which is incorporated herein by reference). A third possibility is to introduce the transfected cells by cannulating one of the five different ducts running from the rete testis to the head of the epididymis, thereby filling the rete and subsequently the tubules (Id.).

The mice are maintained for 2–6 months to allow the transfected stem cells to undergo spermatogenesis. Since A-myb$^{-/-}$ lack spermatogenesis, the presence of mature spermatids and spermatozoa in transplanted mice would indicate successful integration of the rescue construct, and the transgene of interest. The rescued animals can then be mated to produce offspring containing the germ line transgene, or the transgenic spermatozoa can be harvested and used to artificially inseminate females, or to fertilize eggs in vitro.

As an alternative to repopulation of A-myb$^{-/-}$ mice with transfected primary spermatogonial cells, A-myb$^{-/-}$ mice may be infected with retroviruses containing A-myb and the desired transgene. A retrovirus vector is constructed wherein A-myb cDNA is expressed under the control of the A-myb promoter. The structure of one such vector designated pMV-7 Δ ClaI/neo E/H-A-myb, wherein the transgene is the neo gene, is shown in FIG. 9C. Arrows in FIG. 9C indicate transcription start sites. It may be appreciated that the neo gene may be replaced in the vector of FIG. 9C with any transgene which one desires to incorporate into the spermatogonia cell DNA.

High titer viruses are then generated, such as according to the method described by Kozak and Kabat, *J. Virol.* 64, 3500–3508, 1990, incorporated herein by reference. It has been demonstrated that recombinant retroviruses of encoding c-myb cDNA may be generated in titers up to $10^7$ particles/ml (Patel et al., *Mol. Cell. Biol.* 13, 2269–2276, 1993, incorporated by reference). Irradiated packaging cells producing virus, or concentrated preparation of virus, are injected into the testes of anesthetized A-myb$^{-/-}$ mice. Recipient mice are maintained over a period of several months and analyzed for the production of mature sperm and spermatids. The rescued animals can then be mated to produce offspring containing the germ line transgene, or the transgenic spermatozoa can be harvested and used to artificially inseminate females, or to fertilize eggs in vitro.

The present invention also provides treatment methods for restoring fertility in male individuals who are infertile due to a genetic defect in the A-myb locus. Such individuals are characterized by a low level of A-Myb protein, or a loss of functional A-Myb protein. Such individuals may be identified by an analysis of the A-Myb protein size, which will reveal mutations that block A-Myb synthesis, or gene rearrangements which result in production of a truncated protein. Deleterious point mutations which result in a loss of the A-Myb protein's DNA binding ability can be identified by DNA binding assays using synthetic oligonucleotide binding sites as described by Golay et al., *Oncogene* 9, 2469–2479 (1994), the entire disclosure of which is incorporated herein by reference. Alternatively, A-myb cDNA from the afflicted individual may be prepared and sequenced according to conventional techniques, and the sequence compared to the wild-type human A-myb cDNA sequence (SEQ ID NO:5). The A-myb translation initiation codon in SEQ ID NO:5 comprises nucleotides 105–107. The amino acid sequence of the human A-myb polypeptide is set forth as SEQ ID NO:6. As the A-myb gene is expressed in peripheral blood cells, peripheral blood lymphocytes may be conveniently utilized as a source of A-myb DNA for analysis. Methods of sequence analysis aimed at identifying mutations, e.g., the so-called single-strand conformation polymorphism or "SSCP" method (Orita et al., *Genomics* 5, 874–879, 1989, incorporated herein by reference) may be utilized to screen for A-myb mutations.

Local gene therapy is carried out to transfer to the cells of the testes of A-myb defective individuals a construct encoding a functional A-Myb polypeptide. The transfer may be carried out by removing and engineering spermatogonia of such A-myb$^{-/-}$ individuals with a DNA construct designed to express a functional A-Myb polypeptide. The construct preferably incorporates the complete coding segment of the human A-myb cDNA. The engineered spermatogonia are then returned to the testes of the infertile donor. Successful incorporation of the construct results in the production of functional A-Myb polypeptide in the testes of the subject, and production of maturation of competent sperm.

Fertility may be restored in a subject who is infertile due to a defect in the A-myb locus through the use of a retrovirus vector directing the incorporation of DNA encoding a functional A-Myb protein into appropriate cells of the testes. The retrovirus vector is used to infect the testis of the individual in order to obtain the local production of a functional A-Myb polypeptide.

While the functional A-Myb polypeptide which is expressed in the testes according to the aforesaid infertility treatment methods will typically comprise the full-length wild-type A-myb expression product, also included in the scope of the invention is the expression of polypeptides which comprise fragments of the complete naturally occurring gene product, or analogs thereof which differ from the latter by one or more amino acid insertions, deletions and/or substitutions, provided such fragments and analogs are functional in restoring fertility upon expression in the host.

Infertility may be also be treated by the local administration to the testes of an infertile A-myb$^{-/-}$ individual an exogenous functional A-Myb polypeptide. The polypeptide most advantageously comprises the full-length wild-type A-myb expression product, but the functional A-Myb polypeptide may comprise an A-Myb fragment or analog, as described above. Such vehicles may comprise, for example, aqueous vehicles such as normal saline.

The dosage and treatment schedule are selected so as to provide for continuous production of viable sperm at a level which can support successful fertilization.

Also included in the scope of "functional A-Myb" polypeptide is a fusion product comprising the naturally occurring A-Myb polypeptide or analog thereof and one or more attached amino acid sequences which enhance the cellular uptake or penetration of the A-Myb polypeptide into the cells of the testes. Such fusion products may be prepared with resort to commercially available expression vectors which provide for incorporation of DNA sequences of interest downstream from a DNA segment encoding an amino acid sequence having desirable transport properties. The resulting A-Myb fusion protein may be used as the exogenously sourced functional A-Myb protein in treating A-myb$^{-/-}$ individuals for infertility.

Alternatively, a cell-penetrating peptide may be ligated directly to the N-terminal or C-terminal portion of the functional A-Myb polypeptide to enhance uptake. One such peptide is the sixteen amino acid peptide from the third helix of the Antennapedia homeodomain, Arg-Gln-Ile-Lys-Ile-Phe-Phe-Gln-Asn-Arg-Arg-Met-Lys-Trp-Lys-Lys (SEQ ID NO:7) (Derossi et al., *J. Biol. Chem.* 269 (14):10444–10450, 1994). This 16 amino acid peptide, commercially available as "Penetratin 1™" from Appligene, Inc., may be coupled to a functional A-Myb polypeptide according to the manufacturer's protocols (Penetratin 1™, Appligene, Inc., 1177C Quarry Lane, Pleasanton, Calif. 94566).

The practice of the invention is illustrated by the following nonlimiting examples. As it relates to the rescue of nonhuman A-myb$^{-/-}$ animals from infertility by incorporation of a construct encoding wild-type A-myb DNA and a transgene of interest, the practice of the present invention is exemplified using the neo gene, a bacterial gene, as the transgene. The same neo gene also provides for positive selection of transformants harboring an integrated "rescue" construct encoding. It should be understood that neo DNA may be replaced by any other transgene, or that additional transgenes of interest may be included in addition to neo such that the positive selection function of the neo gene product may be retained in screening transformants.

EXAMPLE 1

Preparation of A-myb Knockout Mice
A. Isolation of a Murine A-myb Genomic Clone

The mouse A-myb gene was isolated as follows by screening a λ DASH mouse genomic library derived from the 129/J mouse strain, using a probe derived from the 5' end of the A-myb cDNA clone that encodes the DNA binding domain of the A-Myb protein.

Accordingly, DNA obtained from the tissue of a 129/J mouse (Jackson Laboratories) was digested with the following restriction enzymes: BamHI, EcoRI, HindIII, PstI and XbaI. From a Southern analysis of the digests, the DNA was digested with HindIII to obtain a genomic clone. An approximately 800 bp A-myb cDNA probe was prepared consisting of an EcoRI fragment from the 5' end of the A-myb cDNA spanning cDNA nucleotide positions 1–794 of the A-myb mouse cDNA. The mouse A-myb cDNA nucleotide sequence and deduced amino acid sequence of the A-Myb protein are shown in SEQ ID NO:1 and 2, respectively. The digested genomic Southern blot was probed with the A-myb cDNA probe. A 5.9 kbp Hind III fragment was cloned by size selection in a sucrose gradient followed by cloning into Hind III digested Lambda DASH II phage (Stratagene, LaJolla, Calif.). From the resulting library, the 5.9 kbp A-myb fragment was cloned and subcloned into the pGEM 7Zf(+) plasmid vector (Promega Corp., Madison, Wis.) according to standard procedures (*Molecular Cloning: A Laboratory Manual*, T. Maniatis, E. Fritsch and J. Sambrook, eds. (1982), Cold Spring Harbor Laboratory). The structure of the genomic clone and corresponding restriction map of mouse A-myb is shown in FIG. 1. Analogous to c-myb, A-myb contains three tandem amino acid direct repeats which make up a DNA binding domain. The genomic clone was completely sequenced (SEQ ID NO:3) according to the method of Sanger et al., *Proc. Natl. Acad. Sci. USA* 74, 5463–5467 (1977) and found to contain A-myb exons 3, 4 and 5 (FIG. 1, black boxes). Exon 3 encodes the 5' end of the first repeat of the DNA binding domain, while exon 4 encodes the 3' end of the first repeat and the 5' end of the second repeat. Exon 5 encodes the 3' end of the second repeat and the 5' end of the third repeat. The genomic clone was deposited as NRRL B-21575 on May 1, 1996.

B. Preparation of A-myb Knockout Targeting Vector

To produce a null allele of A-myb, a gene targeting vector was prepared from the 5.9 kbp genomic clone by following the positive-negative selection method which was originally described by Thomas and Capecchi, *Cell* 51:503–512 (1987), the entire disclosure of which is incorporated herein by reference. The vector was designed to disrupt the DNA binding domain of the A-myb gene by insertion of the neomycin transferase (neo) gene into A-myb exon 4 at the ClaI site (FIG. 1).

Accordingly, the Pgk-Neo gene (Mansour et al., *Nature* 336, 348–352 (1988), incorporated herein by reference) was digested with EcoRI and HindIII to yield a 2.0 kbp neo cassette. This DNA fragment was filled by using the Klenow fragment of DNA polymerase I. The genomic clone of A-myb was digested with ClaI, blunt ended and then ligated with the DNA fragment containing the neo cassette. Insertion of the neo cassette results in the disruption of the gene which codes for the DNA-binding domain of the A-Myb protein. The EcoRV/HindIII fragment of this clone was then released by digestion with HindIII and EcoRV, filled using the Klenow fragment of DNA polymerase I and blunt end ligated to the Pgk-TK vector (Thomas and Capecchi, supra) at the HindIII site. The resulting target vector is shown in FIG. 1 (bottom). The orientation of the A-myb, neo and tk genes was determined by restriction endonuclease analysis in conjunction with DNA sequence analysis. The orientation of the neo and tk genes is indicated by arrows in FIG. 1. The neo cassette contained the neomycin transferase gene under the control of the phosphoglycerol kinase 1a promoter and polyadenylation signals. The thymidine kinase gene was flanked by the same promoter and polyadenylation signals.

C. Incorporation of Target Vector in ES Cells

Mouse ES cells (cell line E14a, Handyside et al., *Roux's Arch. Dev. Biol.* 198, 48–55, 1989) were maintained as previously described by Robertson, "Embryo-derived Stem Cell Lines" in *Teratocarcinomas and Embryonic Stem Cells: A Practical Approach*, E. J. Robertson, ed. (Oxford, 1987; IRL Press), pp. 71–112, and cultured in Dulbecco's Modified Eagle's Medium supplemented with 15% fetal calf serum (Sigma Chemical Co., St. Louis, Mo.) and 1000 U/ml of leukemia inhibitory factor on γ-irradiated SNL feeder layers. The above-prepared A-myb knockout targeting vector was linearized with PvuI and introduced into the mouse ES cells by electroporation (250V, 500 mF) as described by Thomas and Capecchi, supra. Following electroporation, the ES cells were plated into 6 cm plates containing G418 (0.1 mg/ml. active ingredient) and 2 $\mu$M ganciclovir. On days 9 and 10 of selection, individual clones were picked, dispersed into single cell suspension in 0.25% trypsin and seeded into two wells, each in a separate 48 well tissue culture plate. After 5 to 7 days, one plate was used for DNA isolation for Southern blot analysis by standard protocols.

Figure 2:
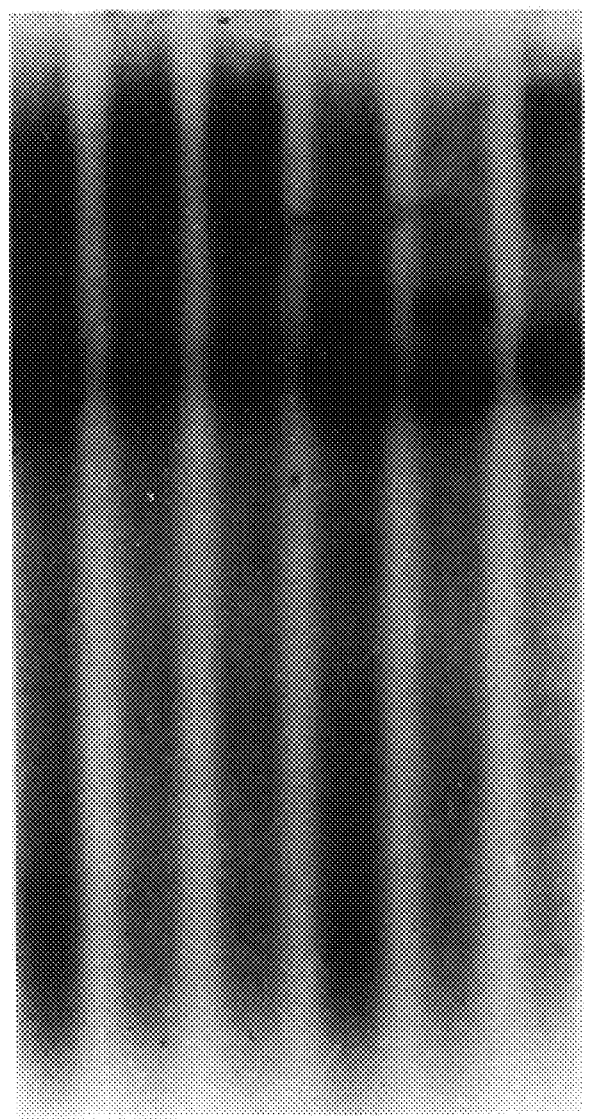
FIG. 2 is a Southern blot analysis of genomic DNA extracts from ES cell clones electroporated with the targeting vector of FIG. 1. The DNA was digested with HindIII, fractionated on an agarose gel, blotted onto a nitrocellulose paper and hybridized with the $^{32}$P-labeled SspI fragment indicated as a black bar in FIG. 1. Molecular weight markers (γDNA digested with HindIII) are shown on the left. Lanes 4 and 5 contain DNA from ES cell clones that contain a disrupted A-myb locus.

DNA was isolated from 87 double resistant clones, digested with HindIII, blotted onto nitrocellulose membranes, and probed with a $^{32}$P-labeled 700 bp SspI 5' A-myb probe. The probe hybridizes to a 5.9 kbp fragment derived from the wild-type A-myb allele, while the targeted locus is predicted to yield an 8 kbp fragment. The results are shown in FIG. 2. The positions of the molecular weight markers (γDNA digested with HindIII) is shown on the left. Lanes 4 and 5 contain the DNA from ES cell clones that contain a disrupted A-myb locus. The appearance of an 8 kbp band indicates a homologous recombination event in two of the 87 clones analyzed. Thus, the mouse A-myb gene was targeted using 4.5 kb of homologous sequence using isogeneic DNA at a frequency of approximately 1 in 40 of the doubly selected clones analyzed.

D. Production of Mouse Chimeras With Heterozygous Null A-myb ES Cells

The two clones bearing a disrupted A-myb gene were microinjected into C57/B6 blastocysts (10–15 cells/embryo), transferred to pseudopregnant foster CD1 females and male chimeras were produced. The chimeras appeared normal and were mated with females from C57/B6 to obtain heterozygous (A-myb$^{+/-}$) mice. The mice appeared normal. Eight offspring with agouti color were produced. Southern blot analysis of DNA derived from tail biopsies of these mice showed that three of them were heterozygous for the A-myb disruption.

E. Production of Homozygous A-myb$^{-/-}$ Null Mice

Figure 3:
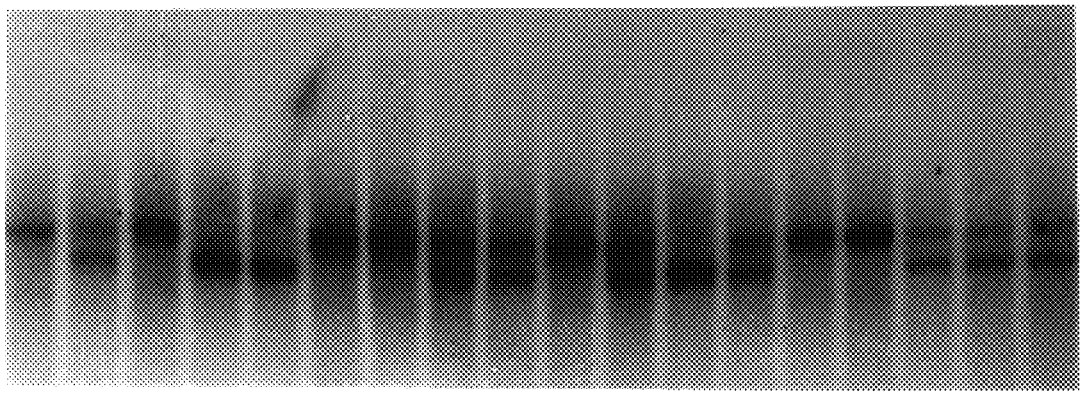
FIG. 3 is a Southern blot analysis of the DNA extracted from tail biopsies of 10-day old pups of A-myb$^{+/-}$ intercrosses, digested with HindIII, and blotted onto a nitrocellulose membrane. The blots were hybridized with the same $^{32}$P-labeled probe as in the previous figure. The A-myb genotypes of the animals are presented above the lanes. A-myb$^{+/+}$ (6 kb); A-myb$^{+/-}$ (6 kb+8 kb); A-myb$^{-/-}$ (8 kb).

Intercrosses were set up between mice heterozygous for the disrupted A-myb allele and progeny were analyzed for A-myb genotype ten days after birth by Southern blot analysis of DNA derived from tail biopsies. The DNA was extracted from the tail biopsies of the 10-day old pups, digested with HindIII, and blotted onto a nitrocellulose membrane. The blots were hybridized with the $^{32}$P-labeled 700 bp SspI probe. Genotyping was determined according to the sizes of the Hind III fragments hybridized (FIG. 3): A-myb$^{(+/+)}$, 6 kb; A-myb$^{+/-}$, 6 kb and 8 kb; A-myb$^{-/-}$, 8 kb. The progeny generated were in the expected Mendellian ratio of 1:2:1 (103:237:91) for wild type (+/+), heterozygous (+/-), and homozygous (-/-) A-myb alleles.

F. Homozygous A-myb$^{-/-}$ Mouse Phenotype (i) Dwarfism

All A-myb$^{-/-}$ pups showed a similar appearance. At birth, A-myb$^{-/-}$ mice appeared to be indistinguishable from their littermates. A difference in size and appearance of A-myb$^{-/-}$ mice was seen during the first few weeks of life. The A-myb$^{-/-}$ pups were runted, wrinkled, and exhibited hunched posture as compared to their littermates. Such an appearance was not observed with the A-myb$^{+/+}$ and A-myb$^{+/-}$ pups. No difference was observed between the heterozygous and wild type A-myb pups. At four weeks, the A-myb$^{-/-}$ pups were approximately 40% the size of their A-myb$^{+/-}$ littermates. As the A-myb$^{-/-}$ mice matured (up to three months), their runted and hunched posture appearance became less pronounced and the mice almost attained the body size (as measured by total body weight) that is comparable to the A-myb$^{+/+}$ and A-myb$^{+/-}$ mice (almost 90% for the females and approximately 70% for the males). However, 25% of the mice do not survive after three to four weeks after birth (23 out of 91).

(ii) Behavioral Defects.

All of the A-myb$^{-/-}$ pups initially displayed the same pattern of altered behavior. These pups exhibit behavioral alterations such as increased hyperactivity (as exemplified by frantic running), trembling upon suspension by the tail, bat and ball postures with hindlimb crossing upon suspension by tail, hunched posture, and inclination to bite handler. Five-six week old males exhibited increased aggressive behavior when mated with female mice for the first time. Females mated with the A-myb$^{-/-}$ male mice had noticeable bite wounds on the genitals, rump, and tail within days after matings were set up. However, older (10–12 weeks old) A-myb$^{-/-}$ male mice do not exhibit this particular behavior during matings even after a period of several weeks. The A-myb$^{-/-}$ female mice have not shown such enhanced aggressive behavior even though they remained hyperactive. All the above abnormal behavioral patterns exhibited by the A-myb$^{-/-}$ mice lessened in severity as the mice matured to 3 months of age. Pathological examination of the nervous system did not reveal any obvious abnormalities in the brain, spinal cord or other structures. However, the possibility of minor neuroanatomical defects that could lead to some of these neurological abnormalities can not be ruled out. While the A-myb$^{-/-}$ female mice are fertile, the A-myb$^{-/-}$ male mice are infertile but are able to copulate as evidenced by the formation of vaginal plugs in the females after mating.

(iii) Body and Testes Size

Figure 5A:
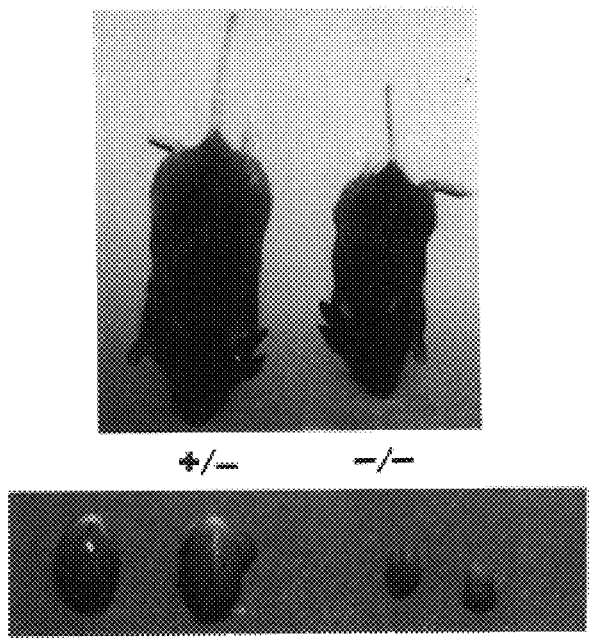
FIG. 5A is a comparison of the total body size and testicular size of 4 week-old A-myb$^{+/-}$ (left) and A-myb$^{-/-}$ (right) mice from the same litter. The testes dissected from the same mice are shown below the mice.
Figure 5B:
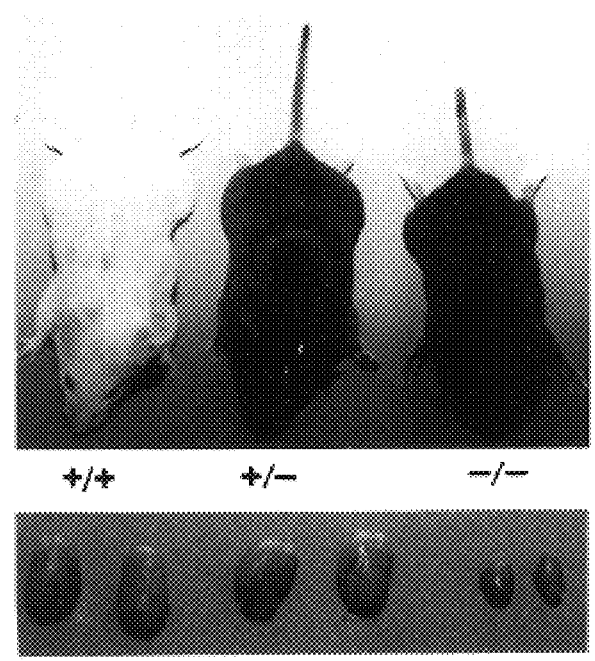
FIG. 5B is a comparison of the total body size and testicular size of 10 week-old A-myb$^{+/+}$ (left), A-myb$^{+/-}$ (middle) and A-myb$^{-/-}$ (right) mice from the same litter. The testes dissected from the same mice are shown below the mice.

FIG. 5A is a comparison of the total body size and testicular size of 4 week-old A-myb$^{+/-}$ (left) and A-myb$^{-/-}$ (right) mice from the same litter. The testes dissected from the same mice are shown below the mice. FIG. 5B is a comparison of the total body size and testicular size of 10 week-old A-myb$^{+/+}$ (left), A-myb$^{+/-}$ (middle) and A-myb$^{-/-}$ (right) mice from the same litter. The testes dissected from the same mice are shown below the mice. The testis of A-myb$^{-/-}$ are atrophic. The size and weight of the testis from the A-myb$^{-/-}$ mice is approximately 25% of their littermates. The small size of the testis is not due to the fact that these A-myb$^{-/-}$ mice are, at least in the initial weeks after birth, smaller in body size as compared to their heterozygous and wild type A-myb littermates (FIG. 5A). When the ratio of testis weight versus total body weight was compared, it became clear that there was a four-fold reduction in the weights of testes derived from the A-myb$^{-/-}$ mice as compared to their heterozygous and wild type litter mates. Even after the male mice attained a more normal weight as a function of age, the testes failed to recover weight unlike other organs and remained in an atrophic state (FIG. 5B).

(iv) Sperm Count

Sperm counts, using whole testis preparations (Amann et al., *Biol. Reprod.* 15, 586–592, 1976), showed that there was a complete absence of spermatozoa in A-myb$^{-/-}$ testes, whereas A-myb$^{+/+}$ mice contained 23.66±1.1×10$^6$ spermatozoa per testis, and A-myb$^{+/-}$ mice contained 22.8+1.26×10$^6$ spermatozoa per testis.

(v) Lack of Spermatogenesis

Figure 6A:
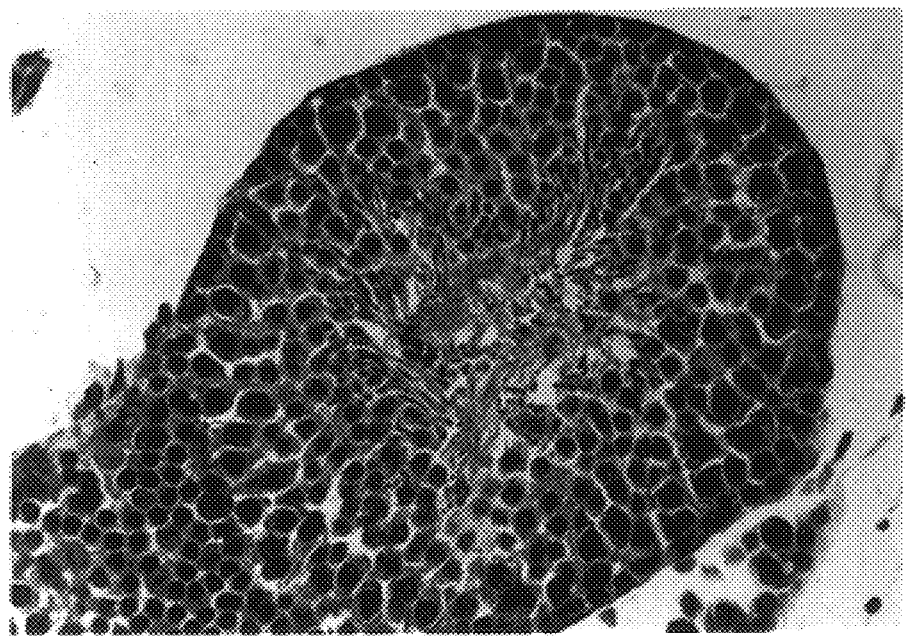
FIG. 6A is a 100× view of a hematoxylin and eosin-stained section of the seminiferous tubules of A-myb$^{+/+}$ mouse testis.
Figure 6B:
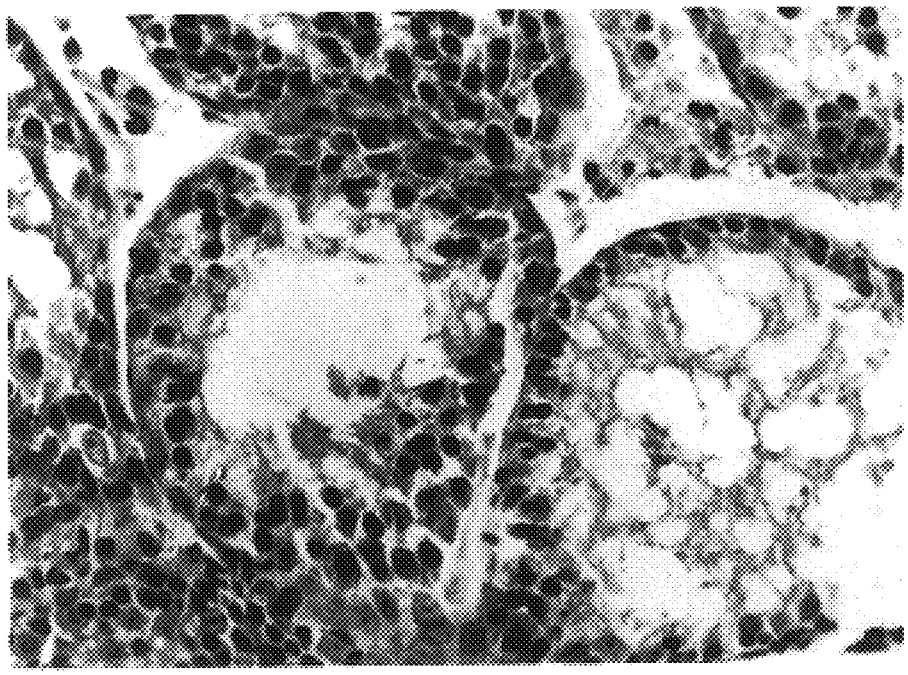
FIG. 6B is a 100× view of a hematoxylin and eosin-stained section of the seminiferous tubules of A-myb$^{-/-}$ mouse testis.

The following pathological analysis of the atrophic testis of the A-myb$^{-/-}$ mice showed a lack of active ongoing spermatogenesis in these mice. Tissues from mutant (A-myb$^{-/-}$), heterozygous (A-myb$^{+/-}$) or wild type (A-myb$^{+/+}$) mice were fixed in 10% buffered formalin overnight, processed and embedded in paraffin using standard procedures. Sections (4–8 μM) were cut and stained with hematoxylin and eosin according to standard procedures. FIG. 6A shows the hematoxylin and eosin-stained sections of the seminiferous tubules of A-myb$^{+/+}$ mouse testes while FIG. 6B shows similar sections from A-myb$^{-/-}$ mouse testis. Magnification is 100 ×.

In the A-myb$^{+/+}$ mice (FIG. 6A), the differentiation of spermatozoa proceeds in a step-wise manner where the spermatogonia are located close to the basement membrane, while cells at progressively later stages of differentiation are situated closer to the tubular lumen. In the center of the tubular lumen mature spermatozoa with tails can be distinguished from other cell types. A-myb$^{+/-}$ mice showed the identical pattern as that of A-myb$^{+/+}$ mice (data not shown).

A-myb$^{-/-}$ mice lack spermatids and mature spermatozoa in the center of the lumen (FIG. 6B). The tubules contain primary and secondary spermatogonia near the basement membrane. A small number of cells with small nuclei, with condensed and possible apoptotic nuclear chromatin are seen in some tubules which represent abortive secondary spermatocytes. The differentiation of spermatogonia seemed to come to an abrupt halt at the pachytene stage of meiosis. Loss of A-myb did not seem to affect the formation of Leydig and Sertoli cell populations as they appeared to be normal in A-myb$^{-/-}$ mice. Thus, the appearance of the small sized testes in A-myb$^{-/-}$ mice is accompanied by the arrest of spermatogenesis resulting in a total absence of mature spermatids and spermatozoa. These results suggest that while A-Myb synthesis is not essential for development primary and secondary spermatogonia, its absence results in a block to spermatogenesis immediately prior to meiosis, at the pachytene stage. When the A-myb$^{-/-}$ male mice were allowed to mate with female mice, they were found to exhibit a normal sexual libido and copulated normally as evidenced by the formation of vaginal plugs in the female mice. But as expected, none of the female mice became pregnant. These results show that the infertility is associated with the absence of spermatogenesis and not an absence of sex-drive. The ovaries of the A-myb$^{-/-}$ female mice appeared normal from histological staining, and as evidenced by the ability of these mice to become pregnant.

(vi) Lack of A-Myb Protein Production in Male Mice

Figure 4:
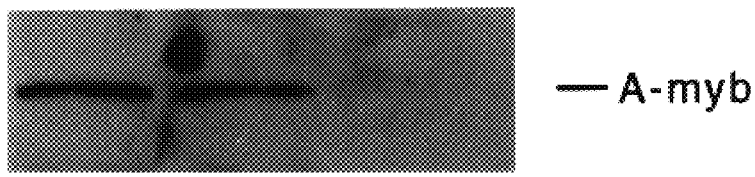
FIG. 4 is a Western blot analysis of extracts prepared from A-myb$^{+/+}$, A-myb$^{+/-}$ and A-myb$^{-/-}$ mouse testes. The blot was probed with a rabbit polyclonal anti-Myb antibody developed by enhanced chemiluminescence. The genotypes of the mouse testes from which the testes extracts were prepared are shown above the lanes.

To verify that the A-myb protein was not synthesized in A-myb$^{-/-}$ mice, Western blot analyses were performed. Since A-myb is predominantly expressed in the testis, homogenates were prepared using testes dissected from A-myb$^{+/+}$, A-myb$^{+/-}$ and A-myb$^{-/-}$ mice. Accordingly, tissue samples were homogenized by Dounce disruption in lysis buffer (10 mM HEPES, pH 7.9; 1 mM EDTA; 60 mM KCl; 0.5% NP40; 1 mM DTT; 1 mM PMSF; 0.5 μg/ml of Leupeptin; 0.5 μg/ml of Pepstatin A and 0.5 μg/ml of Aprotinin), clarified by centrifugation and the protein concentration in the supernatants was determined. Protein samples were separated by SDS-PAGE (10% polyacrylamide) and transferred to nitrocellulose membranes. Membranes were blocked by incubation in PBS containing 2% non-fat dry milk, 2% BSA and 0.1% Tween 20 for 1 hour at room temperature and then rinsed several times in T-TBS (0,05% Tween 20, 20 mM Tris-HCl, pH 7.5, and 150 mM NaCl). The membranes were then incubated with a 1:100 dilution of rabbit polyclonal antibody raised against the DNA binding domain of the Myb protein for 1 hour at room temperature and then rinsed several times in T-TBS. The membranes were then incubated with a 1:1000 dilution of the developing antibody (goat anti-rabbit Ig) for 30 minutes at room temperature and then rinsed several times in T-TBS. The membranes were then developed according to the supplier by chemiluminescence (ECL). A band corresponding to the A-Myb protein in the A-myb$^{+/+}$ and A-myb$^{+/-}$ mouse testis lysates was detected (FIG. 4). The band was totally absent in the A-myb$^{-/-}$ testis lysate (FIG. 4).

Figure 7A:
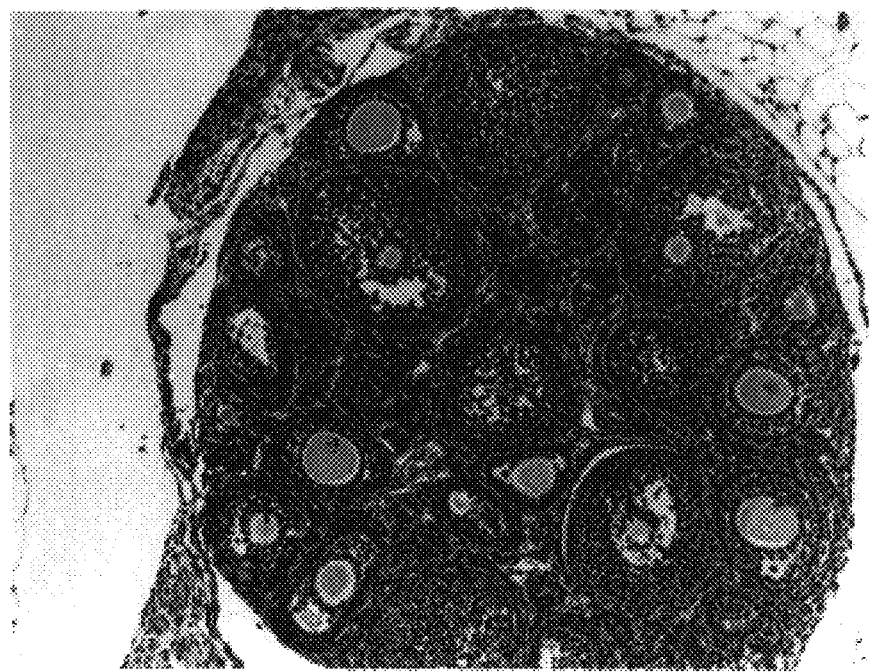
FIG. 7A is a 25× magnification cross-section of wild-type mouse ovaries.
Figure 7B:
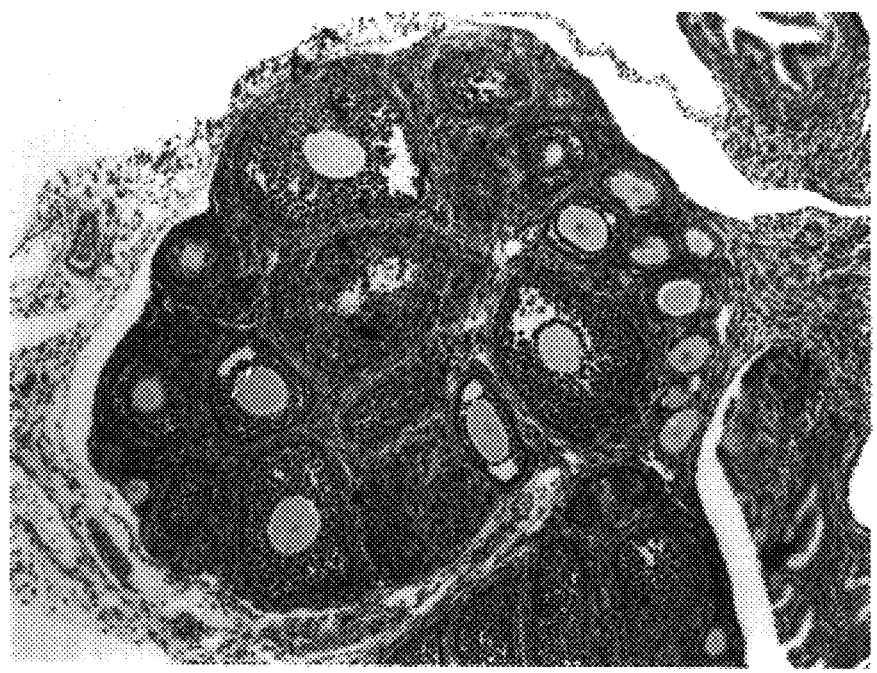
FIG. 7B is a 25× magnification cross-section of A-myb$^{-/-}$ mouse ovaries.

(vii) Defects in the Proliferation of the Mammary Epithelium During Pregnancy of A-Myb$^{-/-}$ Female Mice The ovaries of the A-myb$^{-/-}$ female mice appeared histologically normal. FIG. 7A shows a cross-section of wild-type mouse ovaries while FIG. 7B shows the cross-section of A-myb$^{-/-}$ mouse ovaries. Magnification is 25×. Both cross-sections show normal primary and secondary follicles with normal oocytes. The ovaries of the A-myb$^{-/-}$ mice are proportionally smaller than their A-myb$^{+/+}$ or A-myb$^{+/-}$ littermates.

Figure 8A:
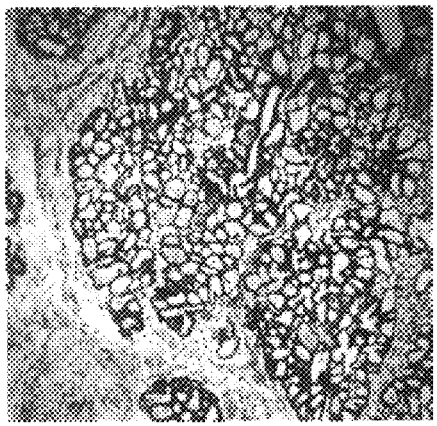
FIG. 8A is a 10× magnification cross-section of A-myb$^{+/-}$ female mouse epithelium, taken from breast tissue of maternal mice two days following the delivery of pups.
Figure 8B:
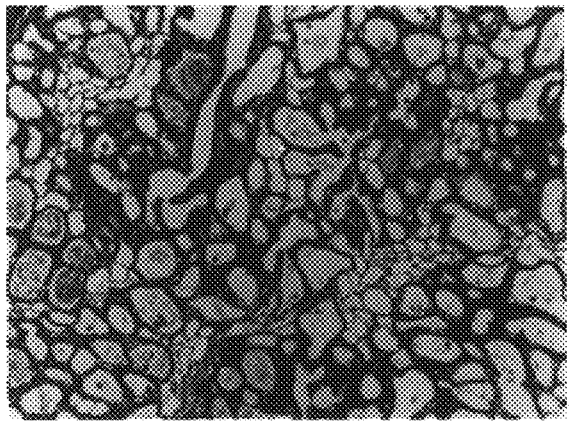
FIG. 8B is a 20× view of the same A-myb$^{+/-}$ tissue of FIG. 8A.
Figure 8C:
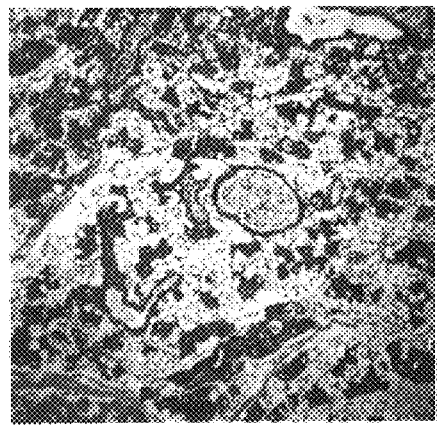
FIG. 8C is a 10× magnification cross-section of A-myb$^{-/-}$ female mouse epithelium, taken from breast tissue of maternal mice two days following the delivery of pups.
Figure 8D:
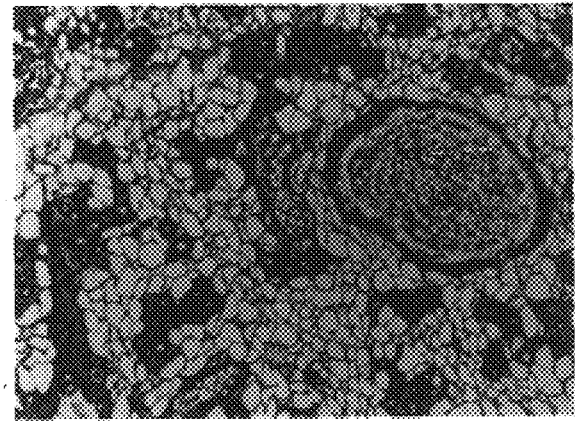
FIG. 8D is a 20× magnification view of the same A-myb$^{-/-}$ tissue of FIG. 8C.

When the A-myb$^{-/-}$ female mice were allowed to mate with wild-type or A-myb$^{+/-}$ mice, they became pregnant and produced litters of normal number. Two days following delivery of pups, maternal female mice were sacrificed and then breast tissue examined for the development of secondary (pregnancy induced) alveolar and lobular growth and development. A dramatic abnormality in mammary function was apparent. A-myb$^{-/-}$ female mice were found to be unable to nurse the pups because of defective mammary tissue proliferation. The mammary epithelium of wild type and A-myb$^{+/-}$ mice underwent a massive expansion following pregnancy (FIG. 8A, 8B), which was considerably diminished in A-myb$^{-/-}$ mice (FIG. 8C, 8D). Specifically, the amount of breast tissue was markedly decreased when compared to a lactating heterozygous mouse. This appeared to be due to diminished secondary (pregnancy induced) alveolar and lobular growth and development (FIG. 8C, 8D). An intermediate lobular pattern was observed, which was closer to a resting lobular pattern. Mammary epithelial ducts from null mutant mice failed to significantly branch and develop alveolar structures which normally cluster together to form lobules that fill the mammary fat pad (FIG. 8C, 8D).

EXAMPLE 2

Preparation of Fertile Transgenic Mice from A-myb Knockout Mice Rescued by Repopulation with Primary Spermatogonial Cells Transfected with A-myb and Transgene A. Isolation of A-myb$^{-/-}$ Primary Spermatogonia Germ cells are isolated from the testis of A-myb$^{-/-}$ mice as follows. Testes from male A-myb$^{-/-}$ mice are removed at postnatal day 10. The tunica are removed from the testes and the exposed tubules are treated with collagenase (1 mg/ml 15 min at 37° C.) followed by trypsin digestion (0.25% for 10 min. at 37° C.). The cells are then centrifuged at 600×g at 16° C. for 5 min. A cell fraction enriched with preleptotene spermatocytes is then isolated by the STA-PUT procedure and unit gravity sedimentation at 4° C. as described by Brinster and Zimmermann, *Proc. Natl. Acad. Sci. USA* 91, 11298–302 (1994). The cells are then resuspended in CMRL-1066 medium supplemented with 80 µg/ml insulin, 3 µg/ml transferrin, 80 µg/ml ascorbic acid and 13% fetal bovine serum.

B. Preparation of A-myb Retroviral Rescue Vector

A rescue construct, encoding a functional A-myb polypeptide and neo as a transgene, is prepared as follows.

1. Preparation of 5' upstream A-myb DNA segment. A 10 kbp HindIII genomic murine A-myb fragment is isolated from a lambda phage mouse genomic library using $^{32}$P-labeled A-myb cDNA as a probe. The 10 kbp HindIII fragment is further cleaved with BstEII to generate a HindIII/BstEII fragment (SEQ ID NO:4, nucleotides 1–3383) which contains the A-myb promoter/enhancer region. A murine cDNA clone containing the A-myb 5'-untranslated region (designated clone 100; Mettus et al., *Oncogene* 91, 3077–3086, 1994)) is isolated from a murine cDNA library using as a probe a 1273 bp HpaII-NcoI fragment derived from the 5'-region of the human A-myb cDNA (Nomura et al., *Nucleic Acids Res.* 16, 11075–11089, 1988). Clone 100 is digested with BstEII and ClaI to form a 0.3 kbp BstEII/ClaI cDNA fragment containing the A-myb 5'-untranslated region (SEQ ID NO:4, nucleotides 3384–3730). The 3.4 kbp HindIII/BstEII genomic fragment containing the A-myb promoter is ligated to the 0.3 kpb BstEII/ClaI cDNA fragment to form a 3.7 kpb HindIII/ClaI fragment (SEQ ID NO:4, nucleotides 1–3730).

2. Preparation of A-myb DNA Coding Segment

A clone, designated pcDNA3_PGC2_A-myb, containing the A-myb coding sequence and a polyadenylation signal from the bovine growth hormone gene, is prepared as follows:

a. Preparation of pcDNA3. Vector pcDNA3.1v (Invitrogen Corp., 3985 B Sorrento Valley Blvd., San Diego, Calif. 92121) is digested with NruI and HindIII to remove the CMV promoter. The ends of the resulting 4.7 kb fragment are filled by T4 polymerase treatment.

b. Preparation of PGK2. A 1.4 kb HindIII fragment is isolated from a PGK2/chloroamphenicol acetyl transferase (CAT) fusion gene, the preparation of which is described by Robinson et al., *Proc. Natl. Acad. Sci. USA* 86(21):8437–41, 1989, the entire disclosure of which is incorporated herein by reference. The 1.4 kb HindIII fragment is blunt ended by T4 polymerase treatment. The fragment contains the human PGK2 promoter.

c. The PGK2 fragment of (b) is ligated into the pcDNA3 fragment of (a) by blunt end ligation. This results in the construct pcDNA3_PGK2.

d. Preparation of A-myb fragment. A construct containing full length A-myb coding sequence in the vector pGEM-37f (Promega Corp., 2800 Woods Hollow Rd., Madison, Wis. 53711–5399) is digested with HindIII and BstEII followed by PvuI and treatment with T4 polymerase (to blunt end the fragment). The 2.6 kb A-myb coding sequence (HindIII/BstEII) is purified.

e. The 2.6 kb A-myb coding sequence of (d) is cloned into the EcoRV-digested pcDNA3_PGK2 construct.

f. The proper orientation of all portions of the final construct, pcDNA3_PGK2 A-myb is verified by sequence analysis.

g. The PGK2-A-myb-bovine polyadenylation fragment (from the pcDNA3 sequence) is removed by AatII/BsaAI digestion and isolation of the 5.1 kb band.

h. The 5.1 kb band is then digested with ClaI and BsaAI to form a 3.0 kbp ClaI/BsaAI fragment comprising SEQ ID NO:4, nucleotides 3371–6775. The A-myb coding sequence constitutes SEQ ID NO:4 nucleotides 3506–6134. The bovine growth hormone polyA signal from the pcDNA3 vector constitutes SEQ ID NO:4 nucleotides 6135–6775.

3. Preparation of Modified pMV-7 Retroviral Vector

The pMV-7 retroviral vector (Kirschmeier et al., *DNA* 7:219–225, 1988, incorporated herein by reference) contains the selectable drug resistance gene neo under the regulation of the herpes simplex virus (HSV) thymidine kinase (tk) promoter and unique EcoRI and HindIII cloning sites for the insertion of cDNAs whose transcription is regulated by the 5' long terminal repeat (LTR). See FIG. 9A for a diagram of pMV-7. To generate a rescue vector in which the A-myb cDNA is regulated by the A-myb promoter, the neo cassette is excised from pMV-7 with ClaI digestion. This neo cassette is then placed in the EcoRI/HindIII cloning site in the pMV-7 vector to form the vector pMV-7 Δ ClaI/neo E/H (FIG. 9B). This vector contains a ClaI site away from the LTR in which the A-myb cDNA may be introduced under the regulation of the A-myb promoter. The 3.7 kbp HindIII/ClaI fragment containing the A-myb promoter and 5'-untranslated region is ligated to the 3.0 kbp ClaI/BsaAI fragment of the pcDNA3_PGK2_A-myb clone containing the A-myb coding sequence and a polyadenylation signal form the bovine growth hormone gene. The resultant 6.7 kbp fragment (SEQ ID NO:4, nucleotides 1–6775) is blunt ended and cloned into the ClaI site (also blunt ended) of the modified pMV-7 retroviral vector, pMV-7 Δ ClaI/neo E/H. The organization of the resultant fully-constructed A-myb retroviral rescue vector, designated pMV-7 Δ ClaI/neo E/H-A-myb, is shown in FIG. 9C.

C. Transfection of A-myb$^{-/-}$ Primary Spermatogonia with Rescue Construct

Primary spermatogonia are obtained from testes of A-myb$^{-/-}$ mice from 5 to 60 days after birth by using a two-step enzymatic digestion protocol as described by Ogawa et al., *Int. J. Dev. Biol.* 41:111–122 (1997). The seminiferous tubules are first exposed by peeling the tunica albuginea from the testes. To disperse the tubules the testes are then incubated in 10 volumes of Hanks' balanced salt solution without calcium or magnesium (HBSS) containing 1 mg/ml collagenase at 37° C. with mild agitation for 15 minutes. The tubules are then washed 4 times in 10 volumes of HBSS, followed by incubation at 37° C. for 5 minutes in HBSS containing 1 mM EDTA, 200 to 700 µg/ml DNAse and 0.25% trypsin with mild agitation. Trypsin activity is then terminated by the addition of 20% volume of fetal bovine serum. Large pieces of undigested material are removed and the cell suspension is filtered through a nylon mesh with 60 µm pore size to remove large clumps of cells. The filtrate is then centrifuged at 600×g for 5 minutes at 16° C. The supernatant is then carefully removed from the cell pellet. The cells are then resuspended in Dulbecco's modified medium containing 10% fetal bovine serum. The cells are then transfected with the A-myb rescue retroviral vector pMV-7 Δ Cla/neo E/H-A-myb. The primary spermatogonia may be transfected by either electroporation (Potter, *Anal. Biochem.* 74:361–373, 1988; Zheng and Chang, *Biochim. Biophys. Acta* 1088:104–110, 1991) or by liposome mediated transfection (Felgner et al., *Proc. Natl. Acad. Sci U.S.A.* 84:7413–7414, 1987), according to the following protocols:

1. Transfection by electroporation:

$5 \times 10^6$ primary spermatogonia are washed with ice cold 1×phosphate buffered saline (PBS) and then centrifuged for 5 minutes at 600×g at 4° C. The cell pellet is then resuspended in PBS at $1 \times 10^7$ cells/ml. 0.5 ml of the cell suspension is then transferred into an electroporation cuvette at 0° C. The A-myb rescue retroviral vector DNA (1 to 10 µg) is added, mixed and incubated on ice for 5 minutes. The cuvette is then placed in the electroporation apparatus at room temperature and is shocked at 1.5 kV at 25 µF. The cuvette is then incubated on ice for 10 minutes. The transfected cells are then diluted 20-fold in Dulbecco's modified medium containing 10% fetal bovine serum and incubated for 48 hours at 37° C. in a $CO_2$ incubator. Stable transfected primary spermatogonia expressing A-myb are then selected for by the addition of G418 (400 µg/ml) to the medium.

2. Liposome-mediated transfection:

$5 \times 10^5$ primary spermatogonia are placed in 6 well dishes and placed at 37° C. in a $CO_2$ incubator overnight. The A-myb rescue retroviral vector DNA (1 to 10 µg) is complexed with the liposome in a polystyrene tube. The DNA is first diluted into 1 ml Dulbecco's modified medium, vortexed for 1 second, and then the liposome suspension (10 µl) TransfectACE (GIBCO/BRL) and vortexed again for 1 second. The suspension is then incubated at room temperature for 10 minutes. 1 ml of the DNA/liposome complex is then added directly to the cells and incubated at 37° C. in a $CO_2$ incubator for 48 hours. Stable transfected primary spermatogonia expressing A-myb are then selected for by the addition of G418 (400 µg/ml) to the medium.

D. Transplantation of Transfected Cells

The transfected cells are transferred into the recipient A-myb$^{-/-}$ mice, according to the protocol as described by Brinster and Zimmermann, supra. The mice are first anesthetized, and under a dissecting microscope, the testes are exposed and immobilized to align the seminiferous tubules with an injection glass pipette (1-mm outside diameter and a 40 µm tip). Small incisions (1–3 mm) are made in the tunica to expose the seminiferous tubules. The tubules are entered with the tip of the pipette and the cell suspension is injected into the tubule. The mice are maintained for 2 to 6 months to allow the transfected stem cells to undergo spermatogenesis. Since A-myb$^{-/-}$ mice lack spermatogenesis, the presence of mature spermatids and spermatozoa indicates that the A-myb transfected into the primary spermatogonial cells is able to reinitiate spermatogenesis in these mice.

EXAMPLE 3

Preparation of Fertile Transgenic Mice from A-myb Knockout Mice Rescued with Retroviruses Containing A-myb and Transgene A vector is constructed by removing the CMV promoter from the vector pMV7 by BamHI/HpaI and inserting the A-myb cDNA with the A-myb promoter at the same site (FIG. 9C). The vector contains the neo gene as the transgene. High titer viruses using the "Ping-Pong amplification method" described by Kozak and Kabat, *J. Virol* 64, 3500–3508 (1990) are generated. Briefly, DNA constructs encoding A-myb are first transfected into Ψ-2 ecotropic packaging cells using calcium phosphate precipitation. Forty-eight hours after transfection, the medium is used to infect PA317 amphotropic packaging cells Miller and Rosman, *Biotechniques* 7, 980–90 (1989), incorporated herein by reference. This method is repeated for 3–4 rounds and at the end of last infection, single cell clones of the virus producing cells are selected using G418 resistance as a parameter of virus titer. Culture supernatants with high virus titer are used to infect the testes of A-myb$^{-/-}$ mice. Accordingly, recipient A-myb$^{-/-}$ mice are anesthetized and the testis are injected with G418 resistant cells previously irradiated and containing A-myb expression vector or concentrated preparations of the virus. The mice are maintained for over a period of several months and analyzed for the production of mature sperm and spermatids by (a) their ability to impregnate female mice or (b) by histochemical analyses.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A transgenic mouse having a genome comprising a homozygous, functionally disrupted A-myb gene, wherein the mouse is an infertile male.

2. A mouse embryonic stem cell having a genome comprising a homozygous, functionally disrupted A-myb gene, wherein said embryonic stem cell is capable of becoming the transgenic mouse of claim 1.

3. A method for generating the mouse embryonic stem cell of claim 2, comprising:
   transferring a targeting construct into embryonic stem cell; and
   selecting for the mouse embryonic stem cell according to claim 2 having the targeting construct integrated into the endogenous A-myb gene of the mouse embryonic stem cell.

4. The mouse embryonic stem cell according to claim 2, wherein said disrupted A-myb gene is disrupted by an integrated targeting construct.

5. The mouse embryonic stem cell according to claim 4, wherein the integrated targeting construct comprises a neo gene.

6. The transgenic mouse according to claim 1, wherein said disrupted A-myb gene is disrupted by an integrated targeting construct.

7. The transgenic mouse according to claim 6, wherein the integrated targeting construct comprises a neo gene.

8. The transgenic mouse according to claim 1 which does not produce A-myb protein.

* * * * *